United States Patent [19]

Keusch et al.

[11] Patent Number: 5,622,168
[45] Date of Patent: Apr. 22, 1997

[54] CONDUCTIVE HYDROGELS AND PHYSIOLOGICAL ELECTRODES AND ELECTRODE ASSEMBLIES THEREFROM

[75] Inventors: Preston Keusch, New York, N.Y.; John L. Essmyer, 230 Columbus Ave., Hasbroucks Heights, N.J. 07604

[73] Assignee: John L. Essmyer, Hasbrouck Heights, N.J.

[21] Appl. No.: 400,273

[22] Filed: Mar. 3, 1995

Related U.S. Application Data

[63] Continuation of Ser. No. 978,434, Nov. 18, 1992, abandoned.

[51] Int. Cl.6 ................ A61B 5/04; A61N 1/04
[52] U.S. Cl. .......... 128/640; 128/641; 128/644; 607/149; 607/152; 252/500
[58] Field of Search .............. 128/635–641, 128/644; 607/145, 152, 153; 252/500

[56] References Cited

U.S. PATENT DOCUMENTS

| | | | |
|---|---|---|---|
| 3,993,049 | 11/1976 | Kater | 128/641 |
| 4,777,954 | 10/1988 | Keusch et al. | 128/640 |
| 4,848,353 | 7/1989 | Engel | 128/640 |
| 4,852,572 | 8/1989 | Nakahashi et al. | 128/640 |
| 4,860,754 | 8/1989 | Sharik et al. | 128/640 |
| 4,989,607 | 2/1991 | Keusch et al. | 128/640 |
| 5,143,071 | 9/1992 | Keusch et al. | 128/640 |
| 5,225,473 | 7/1993 | Duan | 524/388 |
| 5,276,079 | 1/1994 | Duan et al. | 524/386 |
| 5,405,366 | 4/1995 | Fox et al. | 607/152 |

FOREIGN PATENT DOCUMENTS 9113584  9/1991  WIPO ................ 128/644

*Primary Examiner*—Lee S. Cohen
*Attorney, Agent, or Firm*—Kenneth E. Macklin

[57] ABSTRACT

A highly conductive hydrophilic gel comprising a uniform aqueous solution of a crosslinked water-soluble polymer, an amount of a water-soluble electrolyte effective to reduce the transverse electrical resistance of said aqueous mixture to an impedance at 60 Hz less than about 1,000 ohm, which hydrophilic gel also contains a humectant in an amount effective to retard the drying of the conductive hydrophilic gel when it is exposed to the atmosphere while being used. A physiological electrode adapted for providing electrical contact with a surface of a sentient creature and comprising a sheet of the conductive viscoelastic hydrophilic gel.

57 Claims, 3 Drawing Sheets

CONDUCTIVE HYDROGELS AND PHYSIOLOGICAL ELECTRODES AND ELECTRODE ASSEMBLIES THEREFROM

This is a continuation of application Ser. No. 07/978,434, filed Nov. 18, 1992, now abandoned.

This invention relates to improved conductive hydrogels and physiological electrodes and electrode assemblies adapted for application to the surface of any sentient creature, human or non-human, to provide electrical contact with the surface. The physiological uses of the electrode assemblies include both medical and non-medical and veterinary and non-veterinary uses.

BACKGROUND OF THE INVENTION

Medical electrodes comprising a sheet or film of a hydrophilic gel as a conductive member interfacing with the skin of a patient are well known in the art. Hydrogel sheets adapted for use in medical electrode-related applications are commercially produced by, among others in the United States, Promeon, a Division of Medtronic, Inc., (Brooklyn Center, Minn.); Valleylabs, Inc., a Division of Pfizer (Boulder, Colo.); Biostim, Inc. (Princeton, N.J.); Lectec Corp. (Eden Prairie, Minn.); and Conmed (Utica, N.M.).

Numerous U.S. patents disclose hydrophilic gels and medical electrodes employing them. The following illustrate the state of that prior art.

U.S. Pat. No. 3,357,930 (electrically conductive transparent films comprising a polymeric matrix in gel form, a plasticizer therefor, an ionized electrolyte soluble in the plasticizer, and an ionizable solvent, e.g., solid polyvinyl alcohol, glycerine, lithium chloride and silica).

U.S. Pat. No. 3,911,906 (electrode with skin-interfacing film of a pressure sensitive adhesive containing fine electrically conductive particles, e.g., an acrylic copolymer containing carbon powder).

U.S. Pat. No. 3,993,049 (electrode comprising a pliant patch of a formaminated material covered on the side adapted to be placed on the skin with a salt-containing adhesive).

U.S. Pat. No. 3,994,302 (stimulating electrode in which the skin contacting element is an ion-exchange material, e.g., a vinyl pyridine grafted to a polyethylene base).

U.S. Pat. No. 3,998,215 claims an electrically conductive pad which employs a hydrogel impregnated with a fibrous carrier. The polymers disclosed therein as operable require a chemical cross-linking agent. The commercial version thereof sold by the patentee (Minnesota Mining and Manufacturing Co.) has poor skin adhesion and contains bubbles (the latter presumably due to the viscosity of the starting gel and/or the technique employed to impregnate the fibrous carrier with the starting polymer solution). Bubbles in the conductive pad are undesirable because they create local areas of altered electrical properties.

Since the issuance of U.S. Pat. No. 3,998,215, numerous other patents employing a hydrophilic gel as an electrically conducting means which interfaces with the skin of the patient have been issued. The following are illustrative of such patents.

U.S. Pat. No. 4,008,721 (tape electrode comprising a skin-contacting layer of adhesive material, e.g., acrylic copolymer).

U.S. Pat. No. 4,054,714 (electrically conductive adhesive useful for binding together surfaces of electronic devices, comprising a polymeric binder, conductive particles whose surfaces are a noble metal and a normally liquid polyhydric alcohol).

U.S. Pat. No. 4,067,342 (tape electrode for transmission of electrical signals into the body through the skin employing a tape having a surface of a conductive material combined with an adhesive, e.g., acrylic polymer adhesive, and a second surface with the conductive material comprising a magnetic substance).

U.S. Pat. No. 4,094,822 (electrode having a cup, which is taped to the skin, containing a semi-solid adhesive polymeric material, e.g., a mixture of polyvinyl alcohol, boric acid, CMC, glycerol and water and an electrolyte, e.g., AgCl or a zinc salt).

U.S. Pat. No. 4,066,078 (electrode with a skin-interfacing film having adhesive, plastic and hydrophilic properties, e.g., produced from an interpolymer comprising (a) 10–90 parts of an ester of an $\alpha,\beta$-olefinically unsaturated carboxylic acid and a mono- or polyhydric alcohol; (b) 90–10 parts of an $\alpha,\beta$-olefinically unsaturated comonomer; and (c) at least 0.02 parts of a crosslinking agent comprising a difunctional monomer).

U.S. Pat. No. 4,092,985 (disposable electrode comprising an elastically stretchable layer of water-permeable porous webbing permeated with a high water content liquid or semisolid conductive medium).

U.S. Pat. No. 4,109,648 (electrode assembly comprising a self-supporting body of hydrogel, e.g., hydroxyethyl methacrylate polymerized with ammonium persulfate and sodium metabisulfite around graphite fiber).

U.S. Pat. No. 4,125,110; U.S. Pat. No. Re. 31,454 (electrode comprising as a skin-interfacing substrate, a colloidal dispersion of a naturally occurring hydrophilic polysaccharide such as karaya, and a salt in an alcohol as a continuous phase).

U.S. Pat. No. 4,141,366 (electrode for transmitting electrical signals through the skin employing a normally "dry" adhesive which is activated at the time of application by a suitable solvent).

U.S. Pat. No. 4,273,135 (an essentially dry electrode employing as the conductive interface a cohesive, conformable, nonionic hydrophilic synthetic polymer plasticized with a monomer, e.g., glycerol. The electrode is applied to abraded skin wet with normal saline solution or water). This patent contains a detailed description of prior art electrodes.

U.S. Pat. No. 4,274,420 (an electrode similar to that of U.S. Pat. No. 4,125,110 in which the adhesive substrate comprises a karaya gum matrix supporting an electrically conductive fluid).

U.S. Pat. No. 4,300,575 (an electrode with a conductive element composed of karaya, carbon black, isopropyl alcohol and karaya gum conductive solution).

U.S. Pat. Nos. 4,317,278; 4,318,746 and 4,362,165 (electrodes comprising an annulus of foam with an electrode gel in the central region of the annulus, which gel is the subject of U.S. Pat. No. 4,318,746 and is composed of two polymers, one of which is hot water soluble, e.g., kappa carrageenan, and the other is not, e.g., hydroxypropylmethylcellulose, and which contains a potassium salt to enhance the gel's conductivity).

U.S. Pat. Nos. 4,365,634; 4,393,584; and 4,522,211 (electrodes with adhesive layer secured to a semi-flexible plastic-like sheet, and formed from a known electrically conductive adhesive, e.g., Johnson & Johnson Co.'s "Bioadhesive", disclosed in U.S. Pat. No. 4,066,078, or in U.S. Pat. Nos. 4,008,721; 3,998,215; 3,993,049; and 3,911,906; preferably a hydrophilic material disclosed in U.S. Pat. Nos. 3,822,238; 4,156,066 and 4,156,067).

U.S. Pat. No. 4,383,529 (iontophoretic electrode device with a semi-solid hydrophilic hydrated gel formed, e.g., from agar, a protein or a synthetic polymer, e.g., methyl cellulose).

U.S. Pat. No. 4,458,696 (TENS electrode with an extensible interfacing layer of up to 10 mils thickness comprised of a carrier portion coated with an electrically conductive adhesive, preferably a 75:25 butyl acrylate-acrylic acid copolymer neutralized with methyl diethanolamine to which are added a water-soluble plasticizer and tackifier, as described in U.S. Pat. No. 3,065,770).

U.S. Pat. No. 4,515,162 (electrode pad comprising a tacky crosslinked hydrogel adhered to an electrode terminal plate, e.g., a polyacrylic acid and a polyacrylic acid salt, water, and a compound containing at least two epoxy groups, as crosslinking component, and optionally a tackifier, e.g., glycerine, propylene glycol or polyethylene glycol, an electrolyte material, e.g., sodium chloride or potassium chloride, a pH controlling agent, a flexibility imparting agent, an antifungal agent, and the like).

U.S. Pat. No. 4,524,087 (electrode with a conductive adhesive thereon which is a swellable, dermally-nonirritating, conformable, coadhesive, ionic hydrophilic polymer, e.g., produced by UV polymerizing a mixture consisting of triethylene-glycol-bis-methacrylate dissolved in acrylate acid to which is added glycerol and potassium hydroxide in water, using a free radical initiator to initiate polymerization, e.g., a photoinitiator).

U.S. Pat. No. 4,543,958 (electrodes with conductive adhesive film comprising a naturally occurring karaya gum, e.g., available in sheet form from Lectec Corp. or as described in U.S. Pat. Nos. 3,357,930; 3,993,049; 4,066,078; and 4,141,366).

European Published Patent Application 83 305 770.6 (Publication No. 0107376) discloses poly(vinyl pyrrolidone) gel dressings which are non-rigid, sterile, tacky, transparent and absorbent, which have been crosslinked by ionization radiation and which are useful in the treatment of wounds, skin disorders and burns. These gel dressings are formed from 10% to 25%, preferably 15–20% and most preferably 20%, crosslinked poly(vinyl pyrrolidone) and water and irradiated with 1–3 Mrads radiation. Other patents also describe hydrophilic polymers crosslinked into gels, e.g., U.S. Pat. No. 3,998,215 which has poly(vinyl alcohol) as the relevant polymer in concentrations up to 30%.

Furthermore, hydrophilic gels derived from crosslinked poly(ethylene oxide) polymers are described in U.S. Pat. Nos. 3,264,202; 3,419,006; 3,898,143; 3,993,551; 3,993,552; 3,993553 and 3,900,378. These references do not disclose hydrogels with the unique characteristics of the present invention.

U.S. Pat. Nos. 4,750,482 and 4,699,146, both issued to Sieverding, describe irradiating poly(vinyl pyrrolidone) formulations to yield hydrophilic elastomeric adhesives. The conductive formulations contain low molecular weight (300–600 MW) polyethylene glycols as plasticizers for the adhesives and require high doses of irradiation to achieve preferred results. The characteristics of the present invention are not disclosed.

U.S. Pat. Nos. 4,684,558; 4,706,680 and 4,777,954, all issued to Keusch et al., describe tacky adhesive poly(ethylene oxide) gels which may be formulated to also be conductive. The hydrophilic poly(ethylene oxide) solutions are crosslinked by irradiation. These references also disclose the utility of poly(vinyl pyrrolidone) as the crosslinked polymer and include an example of PVP (MW=360,000) in a conductive formulation. Like the Sieverding references, cited above, these patents do not disclose or teach the desirable characteristics possible in the present invention.

U.S. Pat. No. 4,593,053, issued to Jevne et al., describes hydrophilic gel compositions including those comprised of PVP and poly(vinyl alcohol). Chemical crosslinking agents are used, however. Likewise, U.S. Pat. No. 4,192,827, issued to Mueller et al., describes hydrophilic gels which utilize relatively exotic comonomers or copolymers which are not crosslinked by irradiation.

U.S. Pat. Nos. 4,539,996 and 4,554,924, both issued to Engel, disclose conductive adhesive electrodes which utilize adhesive precursors comprised of water-soluble polyhydric alcohols and additional components which are crosslinked via a chemically initiated free-radical process. These patents give no guidance as to the methods of formulation of a cross-linked absorbent flexible adhesive poly(ethylene oxide) (PEO) gel.

Not only does each type of polymer behave differently, even with PEO itself, certain formulations irradiated with a given dose were generally regarded as being non-tacky and non-adhesive. The usefulness of these non-tacky, non-adhesive materials in adhesive applications was believed to be quite limited. Indeed, very few water-soluble crosslinkable polymers can meet all of the requirements of strength, absorbency, flexibility, adhesiveness, and slow drying characteristics possessed by the PEO gels of this invention. Past teachings and uses of crosslinked PEO hydrogel sheets emphasized either the smoothness and ease of removal of the sheet from a surface or the highly tacky adhesive stringy compositions described by Keusch et al. Although the materials used in this earlier work included PEO, the highly desirable properties and characteristics of the PEO hydrogels of the present invention were not recognized.

U.S. Pat. No. 4,989,607, issued to Keusch, discloses a conductive hydrogel comprised of a cohesive uniform mixture of poly(vinyl pyrrolidone), a viscosity-enhancing hydrophilic polymer, and an effective amount of electrolyte.

U.S. Pat. No. 5,143,071, issued to Keusch, discloses adhesive hydrophilic gels comprised of a homogeneous uniform mixture of water and at least one water-soluble high molecular weight polymer. The mixtures may be derived from poly(ethylene oxide) and water or poly(vinyl pyrrolidone), a viscosity-enhancing hydrophilic polymer and water.

The previous teachings on dose versus polymer concentration for PEO in water may be summarized as follows: (1) the dose to achieve a crosslinked PEO hydrogel is inversely proportional to concentration (U.S. Pat. No. 3,419,006); (2) the dose should be greater than 0.52 Mrads (U.S. Pat. No. 3,264,202, claim 6); and (3) at certain doses a tacky adhesive hydrogel can be obtained from a formulation having a given polymer concentration. However, at doses which exceed the levels of (3), above, these same formulations were believed to provide non-tacky, non-adhesive PEO hydrogels of limited utility (U.S. Pat. No. 4,684,558).

Each of these criteria would not be helpful in synthesizing a highly conductive, slow drying PEO gel and would, in fact, be misleading. Poly(ethylene oxide) water systems also have a unique response to high energy radiation. At low concentrations, crosslinking occurs by indirect effects, i.e., initiated with the solvent, whereas at high concentrations (the limit being PEO in solid form) the poly(ethylene oxide) does not crosslink at all. This behavior makes it even more difficult to predict the conditions to achieve effective combinations of absorbency, strength, flexibility, and adhesiveness. Also, the addition of humectants in significant quantities was not addressed and would significantly change the conditions of synthesis.

Although there exist many examples of cohesive and/or conductive hydrophilic gels, none embodies the unique combination of properties disclosed herein. In particular, previous gels were non-tacky and non-adhesive. Yet others may have had tacky, aggressively adhesive, cohesive, or sticky characteristics useful in self-adhesive applications. Yet other formulations yield such a high degree of adhesiveness (i.e., are aggressively adhesive) that skin or hair may be damaged upon removal of the gel sheet. Some hydrogels have a tendency to dry during prolonged use and therefore adversely affect conductivity stability of electrodes incorporating those hydrogels. Consequently, a self-adhesive hydrogel which is more comfortable to use and one which may be formulated to be sufficiently conductive without drying out prematurely during use would be of significant utility.

Hence, none of the currently available hydrogels meet all the criteria of the slow drying adhesive hydrophilic gels of this invention, viz., which are formed from a polymeric material which is dermatologically inert, i.e., one which contains no organic solvents, residual monomer, chemical cross-linking agents or substantial quantities of uncrosslinked polymer, but which contains a humectant; which is a viscoelastic solid, i.e., readily conforms to non-flat areas of the skin; which is sufficiently adhesive to adhere firmly to the skin, so that there is little likelihood of its falling off during use, yet is not so adhesive that it causes pain and/or damage to the skin upon removal; which is adequately adhesive to moist as well as to dry skin and to soiled as well as to clean skin, so that skin pre-preparation with organic solvent or detergent or abrasive is not required; which substantially maintains its water content during prolonged use, thereby making possible electrodes incorporating hydrogels that maintain substantially constant conductivity and do not dry out during prolonged use; which has a good shelf life in a sealed container which does not transmit water vapor through its walls; and whose properties do not readily deteriorate between the time the container bearing the adhesive sheet is sealed and the time at which the container is opened. The adhesive sheets of this invention possess all of these and many other advantageous properties.

SUMMARY OF THE INVENTION

One aspect of this invention relates to a highly conductive hydrophilic gel comprising a uniform aqueous solution of a crosslinked water-soluble polymer, an amount of a water-soluble electrolyte effective to reduce the transverse electrical resistance of said aqueous mixture to an impedance at 60 Hz of less than about 1,000 ohm, which hydrophilic gel also contains a humectant in an amount effective to retard the drying of the conductive hydrophilic gel when it is exposed to the atmosphere while being used.

A process for producing the highly conductive hydrophilic gel which resists drying when used or stored for prolonged periods of time, comprises:

A. forming a uniform aqueous mixture of a water-soluble polymer, an amount of a water-soluble electrolyte effective to reduce the transverse electrical resistance of said aqueous mixture to an impedance at 60 Hz of less than about 1,000 ohm, B. forming the mixture in the general shape and to the dimensions desired, C. irradiating the mixture to crosslink the water-soluble polymer, thereby forming a highly conductive hydrophilic gel, and D. applying to at least one surface of the hydrophilic gel a humectant in an amount effective to retard the drying of the conductive hydrophilic gel when it is exposed to the atmosphere while being used or stored for a prolonged period of time.

The hydrophilic gels of the present invention are substantially free of unbound water, monomers, and crosslinking agents. These gels may be manufactured as sheets with unique surface properties such that the sheets are adhesive and dry out slowly. The adhesive hydrogel sheets absorb preferably at least about twice their own weight in aqueous liquid. Uses of this slow drying adhesive hydrogel, particularly in medical and cosmetic applications, are in the areas of dressings, coverings, face masks, controlled release sheets, surgical drapes, electrodes, tapes and other application areas particularly relating to the skin. Of particular advantage in the slow drying adhesive sheets of this invention are their characteristics of purity and inertness and resultant biocompatibility with human tissue.

Because the present gels dry slowly, they are particularly desirable in long term use medical electrode applications. Also, the preferred adhesive sheets may be produced from high molecular weight poly(ethylene oxide) linear polymers, which are notable for their biological inertness and water compatibility. That polymer, when it is crosslinked by high energy irradiation, contains no crosslinking agents and is free of adhesive additives. Also, the irradiation contributes to hydrogel sheet purity because the irradiated sheets, as produced, are inherently sterile or, at least, contain very low microorganism counts, further adding to the overall purity of the final adhesive product. One of the key features of this invention is that by choosing the proper humectant and quantity of humectant applied to the gel a substantially slower drying hydrogel dressing or hydrogel electrode can be made for long term patient use.

The highly conductive hydrophilic gels of the present invention possess other important characteristics which make these hydrogels especially useful in applications in which these materials are brought into contact with the surface of a sentient being, e.g., the skin of a mammalian subject. In particular, the hydrophilic gels of the present invention are sufficiently cohesive such that substantially no residue remains on the subject's skin after removal of the hydrogel. The hydrogels may also be sufficiently adhesive and possess a sufficient degree of tackiness such that they do not tend to slide off the subject's skin, though the skin be moist; hydrogels are also "non-aggressive," causing no damage to the skin tissue or hair of the subject. Thus, the highly conductive slow drying adhesive hydrophilic gels of the present invention are particularly well suited for use in adhesive electrode assemblies meant to be more comfortable and much more acceptable to the user or medical professional.

In one aspect, this invention also relates to a method of manufacturing a skin-interfacing member of a medical electrode of this invention which comprises subjecting a liquid film of a uniform aqueous mixture, having a viscosity of at least about $2 \times 10^3$ to $2,000 \times 10^3$ cps, of about 0.1 to about 10 wt % of a water-soluble electrolyte, and about 5 to about 35 wt % of poly(ethylene oxide) having a weight average molecular weight of about 200 to about 10,000 kD to an amount of high energy radiation effective to convert the liquid to a sheet of a viscoelastic highly conductive adhesive solid and thereafter forming the thus produced film into a skin-interfacing member of a physiological electrode, and adding a humectant after gel sheet formation and before or after electrode assembly.

This invention also relates to a physiological electrode adapted for providing electrical contact with a surface of a sentient creature and comprising:

a. means for interfacing with a surface of a sentient being comprising a sheet of a conductive viscoelastic hydrophilic gel, wherein the hydrophilic gel is a homogeneous aqueous mixture, substantially free of unbound water, monomers and crosslinking agents, the gel comprising:

i. A uniform aqueous solution of a crosslinked water-soluble polymer,
  ii. a water-soluble electrolyte in an amount sufficient to reduce the transverse electrical impedance of said aqueous solution to an impedance at 60 Hz of less than about 1000 ohm,
  iii. a humectant in an amount sufficient to retard the drying of the conductive hydrophilic gel, to keep it soft and pliable when it is exposed to the atmosphere or being used, and b. a conductive member including means for connecting the physiological electrode to an external electrical apparatus;

said means for interfacing with a surface of a sentient being (a) connected electrically with the conductive member (b) and having a face adapted for interfacing electrically with the surface of the sentient creature to which it is affixed, which gel sheet is more cohesive than it is adhesive to the surface of the sentient creature and is mechanically connected more firmly to the conductive member (b) than it can be adhesively affixed to the surface of the sentient creature, thereby enabling concurrent removal of the conductive member (b) and the means for interfacing with a surface of a sentient being (a) from the surface of the sentient creature after use without leaving a noticeable polymeric residue on the surface of the sentient creature.

In another aspect, this invention relates to a method of transmitting electrical signals from the skin of a person employing a physiological electrode of this invention.

In another aspect, this invention relates to a method of transmitting electrical energy to the skin of a person by employing a physiological electrode of this invention.

In another aspect, this invention relates to an array of physiological electrodes adapted to be placed on the surface of a sentient being, with the individual electrodes prepositioned for easily locating them on the desired areas of the sentient being.

OBJECTS OF THE INVENTION

It is an object of the invention to provide improved conductive slow-drying hydrophilic gels which are comprised of water, a cross-linked polymer, an electrolyte and a humectant.

It is an object of the invention to provide an improved process for producing the improved conductive slow-drying hydrophilic gels which are comprised of water, a cross-linked polymer, an electrolyte and a humectant.

It is an object of the invention to provide physiological electrodes employing as a skin-interfacing conductive member a improved hydrophilic gel which is comprised of water, a cross-linked polymer, an electrolyte and a humectant.

It is another object to provide such an electrode whose hydrophilic gel is biologically inert.

It is another object to provide such an electrode which adheres to the skin when affixed thereto without the necessity of skin pre-preparation, e.g., abrasion or wetting the skin and/or drying with solvent.

It is a further object to provide such an electrode whose adherence to the skin is not adversely affected by the presence of normal amounts of moisture on the skin.

It is a further object to provide such an electrode with superior and stable electrical properties, which is suitable for long term use and which can be peeled off the skin after use without damage to the skin and without having a noticeable polymeric residue.

It is a further object to provide such an electrode whose hydrophilic gel is free of leachable ingredients, e.g., monomers, plasticizers, cross-linking agents, tackifiers, etc.

It is a further object to provide such an electrode which does not readily lose its water content upon exposure to ambient atmosphere or in use on a mammal, e.g., a human.

It is a further object to provide methods for transmitting electrical signals from the skin or electrical energy to the skin employing a physiological electrode of this invention.

It is a still further object of the invention to provide an array of physiological electrodes adapted to be placed on the surface of a sentient being, with the individual electrodes prepositioned for easy positioning on the desired areas of the sentient being.

Other objects will be apparent to those skilled in the art to which this invention pertains.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein:

FIG. 1b is a cross section of a side elevation view of the headband of FIG. 1a;

FIG. 4b is an exploded side view of the replaceable headband electrode sensor module, whose top view is shown in FIG. 4a.

DETAILED DESCRIPTION

Figure 1A:
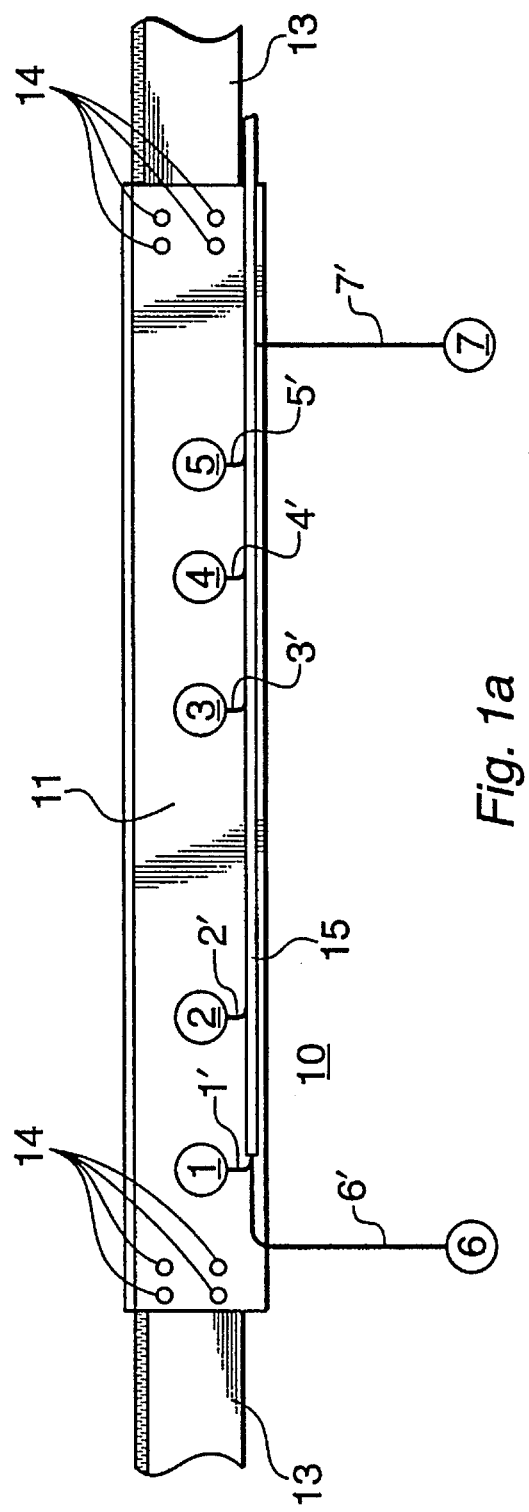
FIG. 1a is a top view of the inside of a headband showing electrodes of the invention placed for forehead and cheek locations.

The highly conductive hydrophilic gels, or hydrogels, of the invention comprise a uniform aqueous solution of a cross-linked water-soluble polymer, an amount of a water-soluble electrolyte effective to reduce the transverse electrical resistance of said aqueous mixture to an impedance at 60 Hz of less than about 1,000 ohm, which hydrophilic gel also contains a humectant in an amount effective to retard the drying of the conductive hydrophilic gel when it is exposed to the atmosphere while being used.

"Hydrogels are crosslinked macromolecular networks swollen in water or biological fluids." That definition is given by Nickolaos A. Peppas in *Hydrogels in Medicine and Pharmaceuticals*, CRC Press (1987).

The crosslinked macromolecular networks may be produced from any water-soluble polymer that is capable of producing a hydrogel. Any water soluble polymer or copolymer or blend of polymers which are crosslinkable is capable of forming a crosslinked hydrogel. The water soluble polymer should also be compatible with the electrolyte and humectant to be employed in the amounts that are desired. Illustrative of the water-soluble polymers that may be used are poly(ethylene oxide), poly(N-vinyl pyrrolidinone), commonly referred to as poly(vinyl pyrrolidone), polyacrylamide, and poly(vinyl alcohol). Preferred water-soluble polymers are poly(ethylene oxide) and poly(vinyl pyrrolidone).

Blends of those polymers and other polymers or copolymers may also be used. An example is a co-crosslinked mixture of poly(ethylene oxide) and poly(vinyl pyrrolidone). In that example both materials may be adhesive polymers. Generally, at least one adhesive polymer can be blended with another non-adhesive polymer in an aqueous salt solution to yield a crosslinked adhesive hydrogel electrode. An example of this is the blend of poly(ethylene oxide) and carboxymethylcellulose. Similarly, a water soluble tacky crosslinkable polymer can be blended with inert fillers and yield a crosslinked, adhesive hydrogel sheet material. In that instance, the major requirement is that the tacky crosslinkable polymer must be the continuous phase in the sheet formed, which requires the wetting out and complete encapsulation of the inert filler by the initial polymer-salt solution.

U.S. Pat. Nos. 3,898,143; 3,957,607; 3,993,551; 3,993,552 and 3,993,553 describe the co-crosslinking of poly(ethylene oxide) with a diverse variety of other polymers. U.S. Pat. No. 3,900,378 describes the crosslinking of a polymer with an inert filler.

To reduce the transverse electrical resistance of the homogeneous aqueous mixtures described herein and consequently, the hydrogels which are produced therefrom, a variety of electrolytic substances may be added to the mixtures in amounts sufficient to produce conductive hydrogels. These electrolytes may be ionizable inorganic salts, organic compounds, or combinations of both. Examples of such salts include, but are not limited to, ammonium sulfate, monoethanolamine acetate, diethanolamine acetate, sodium lactate, sodium citrate, sodium chloride, magnesium sulfate, calcium sulfate, ammonium acetate, magnesium chloride, magnesium acetate, or combinations thereof. Preferably, the electrolyte used is stable and inert upon dissolving in the aqueous mixture and the subsequent radiation crosslinking step. Preferred salts are potassium chloride, sodium chloride, magnesium sulfate, or magnesium acetate. Potassium chloride is most preferred for EKG applications. Although virtually any amount of electrolyte may be present in the mixture, a breakdown in viscosity is observed with too high a quantity of electrolyte. Therefore, the amount of electrolyte should not be so great that it adversely affects the hydrogel and salts out the water-soluble polymer. It is preferable to have the water-soluble electrolyte present at a concentration of about 0.1 to about 15 wt % of the mixture. However, the amount of electrolyte present must be effective to reduce the transverse electrical resistance of the mixture, and the resulting hydrogel, to an impedance at 10 Hz–5 MHz of less than about 1,000 ohms. Typically, about 5 wt % of an electrolyte such as potassium chloride, is sufficient to reduce the impedance at 60 Hz to much less than about 100 ohms.

For example, to impart electroconductivity or physiological salinity to a gel, the electrolyte can be incorporated into the starting viscous solution of the water-soluble polymer, e.g., a linear poly(ethylene oxide), typically an aqueous solution of about 0.1 to 15 wt %, preferably about 0.7 to 10 wt % of a water-soluble salt. Preferably, a dermatologically acceptable metal salt, more preferably in alkali metal salt or alkaline earth metal salt, e.g., sodium chloride, potassium chloride, or a magnesium salt is employed. The specific concentration of the salts depends on the conductivity desired in the hydrogel produced from the solution, generally a transverse electrical impedance at 60 Hz of less than 1,000 ohms, preferably less than 100 ohms, is desired. Such a salt solution may be combined with a water soluble linear poly(ethylene oxide) by mixing to produce a homogeneous viscous solution.

Illustrative of useful humectants are glycerol, sorbitol, a poly(ethylene glycol), propylene glycol, a poly(propylene glycol), an ethoxylated lower fatty alcohol, a propoxylated lower fatty alcohol, and mixtures thereof. The first three illustrative humectants are generally preferred. Most preferred is glycerol. Preferably, the poly(ethylene glycol) or poly(propylene glycol) has a molecular weight of from about 200 to about 600. Preferably, the humectant is incorporated in the hydrogel in an amount effective to retard the drying of the hydrogel when the electrode is being used. A useful concentration of the humectant is from about 2 to about 50 wt %. Preferably, glycerol is present in the hydrophilic gel in amount of from about 2 to about 15 wt %. Generally, there is no advantage in using more than about 13 to about 15 wt %. The humectant may be incorporated in the precursor solution of the hydrophilic gel before it is irradiated, or the humectant may be applied to the gel sheet after it is irradiated. However, adding a humectant such as glycerol to the precursor solution of the hydrophilic gel before irradiation may interfere with crosslinking and may result in toxic substances. Consequently, it is generally preferred to add the humectant after the gel is formed by irradiation of the aqueous solution of the water-soluble polymer. If the humectant is added to the gel after it is irradiated, the humectant is found to be uniformly dispersed throughout the gel in a relatively short time after it is applied to the surface of the gel. It may be desirable to add the electrolyte to the humectant and add both at one time to the irradiated gel produced from the aqueous solution of the water-soluble polymer.

In a specific preferred embodiment of the present invention, the hydrophilic gels are homogeneous aqueous mixtures of water, a humectant and a crosslinked poly(ethylene oxide) (PEO). Not only are they substantially or completely free of unbound water, the advantages of which are discussed herein, they are substantially free of discrete uncrosslinked polymer which could settle, leach or bleed out or otherwise adversely affect the physical properties of the gels.

The preferred poly(ethylene oxide) formulations useful in the applications of the invention include those incorporating and binding high concentrations of water while maintaining adequate surface tack (adhesiveness) and sufficient strength (cohesiveness). The starting water soluble linear poly(ethylene oxide) must have a molecular weight high enough to readily cross-link and form a viscous solution for processing. Generally, polymers with weight average molecular weights from about $0.05–10\times10^6$, preferably about $0.2–6\times10^6$, e.g., $0.54\times10^6$ Daltons are employed. Typically an aqueous solution of about 0.1 to 15 wt %, preferably about 0.7 to 10 wt % of a water soluble salt, preferably a dermatologically acceptable metal salt, more preferably an alkali metal salt, e.g., sodium or potassium chloride is employed, the specific concentration depending on the conductivity desired in the hydrogel produced therefrom. Generally transverse conductives of less than 1,000 (ohm-cm)$^{-1}$ and preferably less than 100 (ohm-cm)$^{-1}$ are desired. Such a salt solution is combined with a water soluble linear poly(ethylene oxide) by mixing to produce a homogeneous viscous solution. The concentration of polymer therein typically is from about 4 to about 35 wt %, preferably about 4 to about 25 wt %, e.g., about 7 to about 12 wt %, of the overall solution, depending upon its molecular weight and the salt concentration therein, i.e., high molecular weight PEO polymers are less soluble in high concentration salt solutions than lower molecular weight PEO polymers. The polymer-salt-water solution should be viscous enough to form into a sheet-like configuration, e.g., a liquid film of about 0.1 to 2 mm thickness, before crosslinking. Illustrative viscosities range from about 2,000 to 2,000,000 cps. The polymer-salt solution is formed into a liquid sheet or film by coating onto a backing film or sheet. If a scrim is incorporated into the body of the solution, the solution should project beyond both faces of the scrim and all surfaces of the scrim should be wet with the solution. This casting technique can be continuous, thereby forming an elongated continuous sheet or film, or discontinuous, i.e., applying individual pools of the solution of a size and shape corresponding to single electrodes. Any quantity of the viscous solution may be applied to a backing film to form a sheet of hydrophilic gel about 10 to about 150 mils (about 0.254 to about 3.81 mm) thick capable of yielding a plurality of individual interfacing means for individual electrodes, or a large single sheet which can be cut up to form a plurality of interfacing means or the sheet can be cut into long strips and rolled into rolls as a tape. The thickness of the aqueous PEO-salt solution that is applied to the backing sheet generally is dictated by the viscosity of the solution and whether or not a scrim is incorporated therein.

These crosslinked PEO polymers and the hydrophilic gels produced therefrom by irradiation with high energy radiation are described generically in U.S. Pat. Nos. 3,264,202 and 3,419,006, whose disclosures are incorporated herein by reference. However, the specific hydrophilic gels employed in this invention are not disclosed therein.

In another preferred embodiment, the hydrophilic gels are a cohesive uniform mixture of water, an electrolyte, a cross-linked poly(vinyl pyrrolidone) (PVP), and a humectant. Not only are these gels substantially or completely free of unbound water, the advantages of which are discussed herein, they are substantially free of discrete polymer particles which could settle out or otherwise adversely affect the physical, or electrical properties of the gels. In fact, the materials of the present invention remain substantially unchanged even after a storage period exceeding one year, under ambient conditions and with properly sealed packages. These materials even retain their desirable physical, chemical and electrical properties for at least one month at an elevated temperature (e.g., at about 500° C.).

The PVP is typically a polymer of N-vinyl-2-pyrrolidone having a weight average molecular weight (Mw) of about 200 kilodaltons (kD) to about 2,000 kD. An advantageous polymer is PVP having a Mw of more than 1,000,000. Homogeneous aqueous mixtures comprising about 5 to about 40 weight percent of PVP are suitable to achieve the objects of the present invention. Preferably, the concentrations of the PVP in the aqueous mixtures are about 10 to about 40 weight percent, most preferably 20 to 35 wt %. The irradiation crosslinking of PVP mixtures are most recently described in U.S. Pat. No. 4,699,146 issued to Sieverding, the disclosure of which is incorporated herein by reference.

The hydrogels and hydrogel electrodes of the present invention may be substantially adhesive or substantially nonadhesive in nature. Generally, those gels made from solutions containing low concentrations of water-soluble polymer and/or low molecular weight polymers will tend to be non-adhesive. The degree of irradiation also affects the adhesiveness of the gels of the invention. Generally, the more the polymer solution is irradiated, the less adhesive the irradiated gel becomes; and the higher the concentration of the water-soluble polymer, the more adhesive the irradiated gel. The practical limitation of the concentration of the water-soluble polymer depends upon its molecular weight, with the higher molecular weight polymer tending to have the lower practical upper limit of concentration. The practical molecular weight-concentration ranges must be found empirically. Factors to be considered in determining practical limits include viscosity and workability of the aqueous solution of the water-soluble polymer and the desired properties, including adhesiveness, of the hydrogel to be produced by irradiation of the aqueous solution of the water-soluble polymer.

The hydrogels of this invention are characterized as being conductive viscoelastic solids which, in the tack rolling ball method (TRBM) test described hereinafter, typically give a rolling ball distance of less than about 10 mm, when the ball employed has a diameter of 16.5 mm, and typically give an adhesion energy force in the Adhesion Energy Density (AED) Determination Test, described hereinafter, of at least about 5 g/cm and not exceeding about 50 g/cm. Notably, these hydrogels also possess a swell ratio (SR) of at least about 2 and a value for the percent gel of at least about 80 pre glycerinated. Moreover, these sheets have greater cohesive strength than adhesive strength, whereby the sheet can be removed from a surface to which it is affixed without leaving a visible residue. Because the sheets of the present gels are integral single structures, much like films of thermoplastic polymers, they have excellent cohesive strength which prevents material from separating from the sheets when they are peeled off the subject's skin.

Because the PEO is cross-linked by high energy radiation, it is free of both residual monomers and chemical cross-linking agents, a very important consideration for a device which is to be affixed to the skin. If desired, the gel optionally can contain preservatives, an anti-fungal agent, a bacteriostat and the like, bearing in mind that unless special steps are taken to incorporate any such agents into the gel after it is formed, e.g., by application of a film of an aqueous solution thereof to one or both faces of the sheet of hydrophilic gel, the materials selected must be able to withstand the irradiation employed to produce the hydrophilic gel.

Other components may also be present in the highly conductive adhesive hydrogels of this invention, if so desired. It is important to keep in mind, however, that one of the advantages of the hydrogels is that they can be prepared with all the attendant properties, and surface characteristics described herein without the need for extraneous chemical crosslinking agents, monomers, and the like. One should therefore incorporate the additive in ways and quantities so that the full benefits of the invention may be realized. In addition, the presence of these additional components may necessitate an adjustment in the dosage of radiant energy applied to the resultant extrudable viscous mixtures to arrive at the hydrogels of choice. This adjustment generally requires further exposure of the multicomponent mixtures to high energy radiation. For instance, additives may be uniformly dispersed in the aqueous mixtures (and, consequently, the resulting hydrogels), which additives comprise preservatives, stabilizers, fire retardants, pigments, refractive particles, antifungal agents, bactericides, antibiotics (e.g., neomycin or silver sulfadiazine), cosmetics (e.g., urea, allantoin, sulfur, anthraquinone, hydroquinones), moisturizers, pharmaceuticals, anesthetics (e.g., benzocaine), antimicrobials (e.g., mercurochrome, silver sulfadiazine, povidine iodine, iodine), healing agents (e.g., collagen), and the like. These additives may be present in individual or total amounts of about 0.001 to about 6 weight percent of the total mixture, preferably not exceeding about 3 wt % in the preinadiated product.

Specific examples of preservatives or "biocides" include, but are not limited to, Dowicil-200®, methyl paraben, ethyl paraben, propyl paraben, butyl paraben, paraben salts, Cosmicil®, glydent germall or combinations thereof. Other formulations for use in topical applications may further comprise boric acid, Burrows solution, and the like.

Generally, the hydrogels of the present invention are produced by exposing an aqueous mixture of least one water-soluble high molecular weight linear polymer to a dose of high energy ionizing radiation effective to form a gel-like material. For example, a homogeneous aqueous mixture of PEO, present at a concentration of at least about 3 to about 35 wt %, preferably at least about 6 to about 18 wt %, may be used. Generally, the lower the molecular weight of the water-soluble. polymer, the greater the percent of the polymer that can be incorporated in the gel. Conversely, the greater the molecular weight of the water-soluble polymer, the less the percent of the polymer that can be incorporated in the gel. Generally, above about 18 wt %, difficulties may be encountered in making or processing the gel. Alternatively, an aqueous mixture of PVP may be employed. It has been found that irradiation of these extrudable viscous aqueous polymeric mixtures produce gels which are cohesive and adhesive.

The concentration of polymer in the solution depends upon its molecular weight and the salt concentration therein, e.g., high molecular weight PEO polymers are less soluble in high concentration salt solutions than lower molecular weight PEO polymers. The polymer-salt-water solution should be viscous enough to form into a sheet-like configuration, e.g., a liquid film of about 0.1 to 2 mm thickness, before crosslinking.

A hydrogel conductive sheet suitable for use in a physiological electrode of this invention can be produced by mixing a water-soluble polymer, e.g., a linear poly(ethylene oxide) with the selected electrolyte and water to form a viscous feed. A convenient procedure is to gradually blend the dry polymer into a solution of the electrolyte in the appropriate amount of water, either at ambient or elevated temperatures. Alternatively, a hot solution of the polymer can be prepared and a concentrated solution of the selected salt slowly blended therewith to achieve the desired or final concentration of electrolyte and polymer. The viscous liquid feed is then applied to a flat surface to form a liquid film thereon, e.g., a film of polyethylene or a polyethylene coated sheet of paper. To contribute to the strength of the hydrogel, both in tension and flexure, a low area-weight scrim can be incorporated into the film during fabrication before crosslinking. The scrim can be of mesh type geometry, either woven or non-woven, e.g., non-woven monofilaments heat sealed together at their interstices or a sheet of thermoplastic polymer with holes in a geometric pattern heat-stamped therein, provided the scrim is of substantial open area and low area weight, e.g., from about 0.1 to 5 mil in thickness and an area weight of about 0.002 to 0.2, preferably about 0.003 to 0.1 $g/inch^2$. Preferably, the scrim and the hydrogel material are present in a range of thicknesses of about 0.125 to about 25 mm. The scrim is preferably fabricated from a natural or synthetic hydrophobic polymer, e.g., a polyethylene, polypropylene, polyester, or polyamide homopolymer. These polymeric materials are preferably nonplasticized so that they cannot leak impurities into the hydrogel.

The resulting liquid film is then subjected to a dose of high energy radiation sufficient to convert said film into a solid gel. To facilitate production, the liquid film is preferably backed on one or both sides with a thin peelable hydrophobic sheet, e.g., polyethylene or plastic coated release paper, before it is irradiated. Either or both plastic sheets are then peelably removable after formation of the hydrogel sheet, either before packaging or before use. The hydrogel sheet, which is now a viscoelastic solid, can be cut to desired size and shape for use as the conductive element that contacts the skin in a fabricated electrode device, e.g., the headband illustrated in FIGS. 1a, 1b, 2, 3, 4a and 4b, described in detail hereafter. Depending upon the application, different types of backing sheets can be used on one or both sides of the hydrogel sheet, e.g., a non-peelable sheet can be used on one side only or a peelable sheet on one side and a non-peelable sheet on the other.

After the viscous solution is applied or cast to the desired thickness, it is then subjected to crosslinking high energy irradiation, such as a high energy electron flux as produced by an electron accelerator. If conditions are selected which exclude atmospheric oxygen, gamma radiation may be used. The major requirement is that the beam of electrons be of sufficient energy to completely penetrate the solution, so that the solution receives a radiation dose effective to crosslink the entire cross section of the sample. Proper dose/energy/thickness relationships are readily available to those skilled in the art of radiation processing and therefore need not be discussed in detail. To achieve the desired degree of uniform crosslinking, i.e., effective to convert the viscous polymer solution into a viscoelastic solid gel, doses typically of about 0.20 to 5.0 Mrads and usually about 0.75–2.0 Mrads are required, depending upon the selected polymer molecular weight, and its concentration. If selected functional or therapeutic additives are included in the viscous polymer solution, the radiation dose may be further shifted within this range. Generally speaking, higher polymer concentrations require high irradiation doses to produce an acceptable viscoelastic solid gel than lower polymer concentrations.

After the conductive hydrogel sheet is irradiated and converted into a viscoelastic solid, it can then be incorporated into an electrode. First it is cut to size, if it is not formed in its desired final shape. If both faces of the hydrogel are covered with backing material, one of its faces is freed from the backing material. The side freed from the backing material can then be coated with a humectant such as glycerol if it is not already incorporated in the hydrogel. That side is then affixed to a non-porous support conductive member, e.g., a material which contains a conductive metal button, snap, or tab of conductive foil-polymer laminate which is capable of receiving an electrode lead wire and connector to an external electrical apparatus. The electrode is then ready to be packaged. The final package preferably is a gas, moisture and microorganism impermeable sealed pouch or envelope, e.g., formed by heat sealing a heat sealable aluminum foil polymer laminate.

When a packaged electrode is ready for use, it is removed from its package, the remaining backing material is released by peeling it from the gel interfacing sheet, and it is applied to the skin of the person. The electrode lead wire is then attached to the electrode at the fastener conductive member. Alternatively, the lead wire can be attached to the electrode before the remaining backing material is removed, the backing material then removed and the electrode with the connecting wire attached applied to the skin. Alternatively, the packaged electrode can be provided with its own electrode lead wire already attached. The same sequence of backing material removal and application of the electrode to the skin would then apply without the necessity of attaching a lead wire to the electrode before or during application.

The hydrogel interfacing member of the electrodes of this invention have high adhesive strengths, which means that they can readily be affixed to the skin and will adhere thereto with little risk of accidentally dropping off through loss of adhesion. Because the interfacing member is water based, it is relatively immune to the effects of moisture on the skin and will not slide off as a result of perspiration forming under the electrode while affixed to the skin. They also have high cohesive strengths, which means that they can be removed from the skin after use without leaving any visible residue. Interestingly, although the gels have a high adhesive strength, it is not high enough to pull hairs from the skin or otherwise damage the skin when the gel is removed therefrom.

The physiological electrodes of this invention containing a sheet of a hydrophilic solid gel, as disclosed herein as a skin-interfacing member, can assume a wide variety of shapes and construction, which are within the knowledge and skill of the practitioner in the art.

Because the hydrogels will lose water eventually under ambient conditions, they are preferably stored in a water and gas impermeable container, e.g., a polyfoil packet formed from the laminated plastic conventionally used to store measured amounts of freeze-dried or ground coffee. Sealed envelopes are conventionally produced by heat sealing a pair of sheets of thin plastic around the hydrogel sheet-backing laminate, or physiological electrode in which a hydrogel sheet is mounted, or by heat sealing the open end of an otherwise sealed packet or envelope formed from a single sheet of the laminate.

If the film or sheet of hydrogel is to be stored separate from the components of the physiological electrode with which it is to be used, both faces thereof are preferably covered with a sheet of peelable release liner, e.g., polyethylene. If the sheet of hydrogel is to be stored mounted in the physiological electrode with which it is to be used, its exposed face, i.e., the face to be applied to the skin, is covered with such a release liner. If both faces are covered with a release liner, optionally different liners can be employed, one of which is more readily removable therefrom than the other, e.g., a sheet of polyethylene covering one face and a sheet of "Mylar" polyester covering the other, thereby ensuring that a predetermined face of the film or sheet is exposed first. In some end use applications, one of the faces of the film or sheet is covered with a conductive liner which is not removable and is used as a conductive member in the final electrode assembly. Other variations should be evident to the skilled practitioner.

The present hydrogel sheet or film can be packaged singly or in multiples between the release liner or liners. In TENS end uses, it is desirable to mount a plurality of spaced apart circles, squares or rectangles of the film or sheet of the hydrogel on a plastic sheet, e.g., a 2 mil film of "Mylar" polyester and cover their exposed face with a different release liner, e.g., a 2 mil film of polyethylene or a sheet of polyethylene coated paper release liner. Either or both of the facing films can be appropriately scored to facilitate removal of the units of hydrogel sequentially. If desired, one face of a plurality of units of the hydrogel can be covered with a large backing sheet, one facing film which is unscored and the other face covered with a release liner of the same dimensions as the units of the hydrogel so that a unit of the hydrogel and the latter release liner can be peeled off together, one at a time from the large backing sheet.

In another embodiment, a large sheet of a laminate formed from the hydrogel and films of plastic covering its faces, e.g., a film of polyethylene on one face and a film of Mylar polyester on the other, is scored at spaced intervals in both directions thereby producing a plurality of severable square or rectangular units of the laminate, each for use individually in conjunction with a physiological electrode by tearing the laminate along a pair of perpendicularly positioned lines, thereby releasing a unit of the laminate from the sheet.

When the sheet of conductive hydrogel is of the same dimension as a release liner covering an exposed face thereof, removal of the latter is facilitated if the latter is slit into pieces, thus providing an edge which can be easily raised with a fingernail or tool.

If desired, a plurality of circles, squares or rectangles of the hydrogel with a release liner covering one face can be "stacked" one upon the other so that a column of such units of the hydrogel sheet with both faces covered with a release liner is formed. Desirably, in such an arrangement, one side of the release liner has a higher adhesive value than the other, so that only one unit of the hydrogel is removed at a time from the column. Such columns can be conveniently stored in glass jars or aluminum lined paper tubes with a moisture impervious cap which form a gas and moisture impervious sealed container.

The manner in which a hydrogel film of this invention adheres to the skin is an important aspect of this invention. The hydrogel adheres sufficiently to dry, damp, clean, or soiled skin. It is tolerant to perspiration which forms from the skin under the hydrogel after the electrode is applied to the skin, because the hydrogel can adsorb a substantial amount of water before it loses its surface tack. Conversely, because it is 65%+water, it does not create chemical bonds with the skin and hair which results in pain and/or skin damage when an electrode employing a conventional adhesive-based skin-interfacing member is removed after use.

To test for skin adhesiveness, samples of the hydrogel with backing removed from one side can be applied to the skin and left on. This step is done both with the scrim-containing hydrogel films alone and with a scrim-containing hydrogel film attached to a support backing bearing a metal conductive snap electrical terminal. How well the hydrogel adhered to the skin is then observed and how easily the electrode material can be separated from the skin is noted, along with whether or not any residue is left on the skin.

The adhesiveness and tackiness of the conductive hydrogel sheet or films can be quantified by the "Tack Rolling Ball Method" (TRBM) as specified by the Pressure Sensitive Tape Council. This test method for adhesive materials is detailed in The American Society for Testing Materials, Designation D3121-73 (Re-approved 1979) which test method is under the jurisdiction of ASTM Committee D-14 on Adhesives. The test utilizes an inclined trough which can be obtained through the Pressure Sensitive Tape Council, 1201 Waukegan Road, Glenview, Ill. 60025, that is equipped with a release lever at the top through which a 16.5 mm diameter, 21.7 g steel ball is released onto the trough. The ball gains momentum as it descends the incline and rolls onto the adhesive surface whose adhesiveness is being measured, the shorter distance the ball travels thereon, the higher the adhesion value. In some cases, an 11 mm diameter, 5.6 g ball is used also.

The test is performed as follows: Remove the backing materials from both sides of a hydrogel sample cut one inch wide and at least three inches long. The test is run in a controlled environment (72° F.±5° F. and 50%±10% relative humidity). A hard, horizontal surface of sufficient size to conduct the test is selected. Both metal and glass plates have proved satisfactory. Before testing each adhesive sheet, clean the inclined trough thoroughly with isopropanol.

The specimen to be tested is placed flat, adhesive side up, in line with the inclined trough. The end of the specimen opposite the incline is held to the table. Only one test is run on each specimen. Each time before the ball is rolled onto the hydrogel, it is thoroughly cleaned with distilled water, isopropanol, or another appropriate solvent, which removes any residue that might otherwise remain from a previous test, and then wiped with a lint-free, bleached, absorbent material to remove any remaining residue. After being cleaned, the ball and raceway are not touched. Clean, dry tongs are used to place the ball on the upper side of the release. The ball is released, and it will roll to a stop on the adhesive material. The distance from the point where the ball initially contacts the adhesive to where the ball stops is measured. The average of the stopping distance measurements of five or more tests is recorded. Pertinent additional comments based on visual inspection such as noticeable residue on ball, lift of adhesive from substrate, etc., are noted.

Another test that quantitatively measures the extent of crosslinking in a polymeric mixture involves an extraction test. This test provides % gel values and is carried out substantially as described below. A two inch by two inch piece of PEO gel and weighing about 2.5 grams is extracted with 200 ml of distilled water for 72 hours at ambient temperature. The excess water is then removed from the swollen sheet which is then weighed. The swollen sheet is then baked in a 50° C. oven for 24 hours. The resulting desiccated gel is then weighed. The ratio of the "dried" gel weight over the original weight of the polymer in the sample is the gel fraction or % gel. Preferred hydrogels of the present invention have % gel values of at least about 80 percent.

Another important feature for an adhesive sheet especially one that is intended for utilization in wound management applications is its absorptive capacity. This property is important because an adhesive on the skin can readily lose its adhesive bond due to a layer of perspiration accumulating at the interface. Moreover, if an adhesive material is utilized as a wound dressing it must be capable of absorbing the exudate from the wound, as this is one of its primary functions. If the gel cannot do so, it will also lose its adhesive bond and move from the site where it was intended to function. For these reasons it is very important for the adhesive sheet to have good equilibrium or absorption capacity for aqueous liquids. A test method that quantitatively measures the absorption capacity of a crosslinked polymer system is the swelling test.

The test method proceeds in exactly the same manner as the extraction test previously mentioned, up to the point of extraction. The weight of the extracted sheet, with unbound excess water removed from the surface, divided by the weight of the original sheet is the swell ratio (SR). In the hydrogels of the present invention, it has been discovered that the preferred embodiments which are highly conductive and adhesive are those which have an absorptive capacity, as measured by the swell ratio (SR), of at least about 2.

Another test to measure relative strength and stickiness of an adhesive bond is the Adhesion Energy Density Determination test. This test measures how well a hydrogel sheet adheres to a flat surface. The adhesion energy which is measured is the combined strength of the surface bond of hydrogel sheet to the flat surface and the strength of the hydrogel sheet itself (i.e., a combined cohesiveness/adhesiveness test).

A sample of the hydrogel sheet to be tested is placed unbacked on a clean flat stainless steel block. The block in turn is placed on a block of flexible foam, which in turn is placed on a test stand. With the setup in place, a steel ring is placed on top of the test sample and aligned with the test probe to be used so that the latter will descend therethrough without touching the ring. A cylindrical (1 inch diameter) polymethylmethacrylate test probe then descends into the sample at a constant rate to a constant depth. (In the hydrogel films tested, the descent rate is set at 0.5 mm/sec. and the penetration is set at 1.0 min.) Before the test probe is made to descend, it is cleaned with isopropanol or distilled water and dried with a lint-free cloth, to make certain no residual adhesive material is on the face of the probe before the test is begun. All tests are run at 72° F.±5° F. and at a relative humidity of 50%±10% and each test sample is stored at these conditions for at least one hour before the test. When the test probe has achieved 5 grams force, it then descends 1 mm into the hydrogel sheet and begins its return (at a rate of ascent of 0.344 cm/sec), the adhesive sample being tested has adhered to the face of the test probe. From the start of the return of the probe to complete separation of the test sample from the face of the probe, the force on the probe and the corresponding displacement is recorded using a Voland Stevens LFRA Texture Analyzer and Recorder (Voland Corporation, Hawthorne, N.Y.). The area under the force-displacement curve is the adhesion energy. For the 1.0 inch diameter probe used, it is the adhesion energy per 5.07 $cm^2$, which is the adhesion energy density (AED). For the values referred to herein, the force was measured in grams and the displacement measured in centimeters so that adhesion energy densities are reported in $g-cm/cm^2$.

The improved physiological electrodes of the invention may be applied to the surface of any sentient creature, human or non-human. The non-human creatures may be mammals or non-mammals. The electrodes may provide electrical stimulus to the surface of the creature, detect microcurrents from the surface of the creature, or conduct both functions sequentially or concurrently. For convenience in describing the invention and because of the importance of the human applications of the invention, the following description will refer to uses for humans. However, the invention can be used in similar manners for non-human creatures, particularly mammals.

The electrodes may be used singly or in an array of two or more electrodes spatially arranged on a substrate, particularly a flexible substrate, so that the array of electrodes may be set in place on a person's skin in one action and yet place the electrodes in precise relative positions on the skin.

The hydrophilic gels employed in this invention are unique in that although they are electroconductive, they are substantially free of unbound water. This is an important property for several reasons. First, it means that the gel does not "bleed" free water under the influence of pressure and/or elevated temperatures, which bleeding can adversely affect one or both of adhesiveness and/or uniformity of conductivity. Second, it means the gel is not "broken" if subjected to temperatures below the freezing point of water. This is very important from a storage and shipping stability point of view. Finally, it renders the gel more resistant to "drying out" after being removed from its sealed gas and moisture impermeable package and during extended use. These gel integrity characteristics are enhanced by the addition of humectants.

Because sheets of adhesive hydrogel and physiological electrodes, particularly those used for medical purposes may have to be sterile, the packaging of the electrode should ensure such sterility. Although this cannot conveniently be achieved conventionally by autoclaving, since this could adversely affect the polymer or alter the moisture content of the gel, sterility can readily be accomplished by other means, e.g., with ethylene oxide or by packaging the electrode as an integral part of the high energy radiation step of converting the starting liquid polymer solution to a solid hydrogel, which effectively sterilizes the hydrogel and associated structural and packaging materials.

The electrode assemblies according to this invention are suitable for application to skin in connection with both electrical signal sensing physiological electrical apparatus and electrical energy transmitting physiological electrical apparatus, i.e., they can be used both as sensing electrodes and as working electrodes.

Examples of "sensing" electrodes are those used in electrocardiogram (ECG), electrooculogram (EOG), electrogastrogram (EGG), surface electromyogram (EMG), electrodermal responses (EDR), electroencephalograms (EEG), visual evoked potential (VEP), and auditory evoked responses (AER). Moreover, because the hydrogels employed therein are biologically inert, the assemblies according to this invention are suited to the detection of signals requiring application to or implanted within sensitive areas of the body, such as the cornea in the electroretinograms (ERG), or in body cavities where the materials of conventional assemblies may prove unsatisfactory, such as in the summated electrocochleograms (ECOG), electro-olfactorograms (EOG) and measuring electrovaginal potentials (EVP).

The electrodes of the invention are particularly useful in an eye-controller headband that is illustrated in FIGS. 1a and 1b, 2, 3 and 4a and 4b, described in detail hereafter. The electrodes of this invention located at specific spots on the headband and those on the cheeks sense the eye movements of the person wearing the headband. The eye-controller headband can be used for hands-free computer input instead of a computer mouse, thereby eliminating the need for the mouse and a mouse pad and also eliminating the muscle and back pain resulting from prolonged uncomfortable use of a mouse. The eye controller can be used (a) to play video games, (b) for word processing, (c) as an aid for the physically disabled, and (d) in conjunction with virtual reality systems. With appropriate computer programs, the eye controller can be used to accomplish a wide variety of tasks, such as playing music, assisting in medical rehabilitation, controlling robotics, developing athletes and training movements, operator performance monitoring, and the like.

Examples of "working" electrodes for which the electrode assemblies of this invention can be used are those adapted structurally for Transcutaneous Electrical Nerve Stimulation (TENS), use as an Electro-Surgical Unit (ESU), for External Cardiac Pacing (ECP) and for Defibrillation (DEFIB).

The physical, electrical and chemical characteristics of these two general types of electrodes, plus three subcategories of the latter type, are set forth in Table I, below.

TABLE I

| Electrode type | Size in.$^2$ | Thickness (mils) | $H_2O$ Content | Resistance ohms-cm |
| --- | --- | --- | --- | --- |
| Sensing | 0.25–1.5 | 20–75 | 80–98 | 3,000-10 |
| Working | 0.5–50 | 50–115 | 80–98 | 50,000-1 |
| Defib. | 4.5–25 | " | 90–97 | 5,000-15 |
| ESU | 5.5–50 | " | 80–95 | 50,000-1 |
| ECP | 12.5–25 | " | 80–93 | 3,500-15 |

General Characteristics of Hydrogel Interfacing Member

The following is e summary of the properties of the hydrophilic gels of this invention.

Biocompatibility

The hydrophilic gel is inert and is not metabolized. It has a normal pH of about 7, which is allowed to "float" between 6 and 8. The gels have a zero irritation index. Because it is produced by irradiation, the gel is virtually or completely sterile, with less than 10 colonies per cubic centimeter (the measurable limit).

The hydrogel contains no extraneous or other objectional ingredients. It does not contain extraneous chemicals such as monomers and cross-linking agents, which are present in chemically linked cross-linked gels, or solvents, etc., which are an integral part of formulated adhesives. All ingredients have proven bioacceptability on contact with the skin. Normal exudants flow into the matrix of the gel away from the user's skin. Its hydrophilic properties eliminate the common requirement for abrasive treatment and/or other significant skin preparation.

The biocompatibility of the hydrogel, i.e., its hypoallergenic properties, was tested in accordance with the method described in the Federal Hazardous Substances Act (modified somewhat in accordance with the draft protocol for Dermal Toxicity Testing for Medical Devices in Contact with Skin). An irritation index of zero was returned when tested on abraded and unabraded skin of New Zealand white rabbits.

Specific Ion Control

Experience has shown that specific ion control with even distribution within the conductive matrix is of paramount importance in electrode performance. The precise ion level and dispersion in the process employed to produce the hydrogel lends itself perfectly to the production of a unique family of controlled conductive-adhesive transmission components. Although the polymer matrix theoretically could hamper ion mobility, the volume resistivity of the hydrogel remains low. The electrolyte may be added to the solution of the water-soluble polymer and water before irradiation or may be added to the surface of the gel after irradiation. In the latter case, after a relatively short period of time, the electrolyte is evenly dispersed throughout the gel.

Hydrophilic Characteristics

The hydrogel contains no free water. The water in the hydrogel is an integral part of the gel structure and therefore cannot be separated therefrom by physical means such as pressure. Thus, the crosslinked matrix remains homogeneous under gravity and even at temperatures approaching freezing water. Its imbibing property enables the hydrogel to cleanse the body surface of water soluble exudates and secretions by drawing them up into the gel by osmosis, thus lowering the skin irritation factors commonly associated with other organic polymers. The gel pad has a distinct advantage of conforming itself to the irregularities of human skin, producing a substantially uniform contact. This characteristic is important because poor skin contact can cause electrical noise or current loss, which can change the accuracy of a biopotential recording or the efficacy of an electrical energy treatment. In addition, the generally low-noise and low current loss electrodes of the invention allow more useful information to be imparted to or derived from the electrodes. For example, when gathering data from the surface to be processed, it is possible that the higher signal/noise ratio will allow more information to be determined because of higher resolution. Because of the high water content, it is generally not necessary to prepare the skin by shaving it, which some commercial electrodes require. The high water content also precludes the necessity of preparatory skin shavings which many commercial electrodes require.

During prolonged exposure to air or prolonged use, the prior art hydrogels may exhibit a tendency to dry out to an undesirable extent. Therefore, a humectant is incorporated in the hydrogel of the invention in an amount effective to retard the drying of the hydrogel.

Normal human skin is relatively conductive. However, extra dry skin may be relatively non-conductive, i.e., it may function as an insulator to the passage of the electrical signal to the electrode being used. It has been found that the glycerol added to the electrodes of the invention surprisingly improves the signal transmission apparently because the mixture of glycerol and water wets the stratum corneum better than water alone.

Adhesive Properties

The hydrogels' adhesive characteristics are manifested in their ability to conform to minute irregularities on the surface on which they are placed, while retaining their cohesive properties. These characteristics meet the criteria of a adhesive, without the necessity of additional chemicals. The degree of adhesion to a given surface is a function of the degree of irregularity or porosity of the surface. The hydrogels retain their adhesive quality even while absorbing normal perspiration. The viscoelastic properties of the hydrogel within the gel structure allows it to flow into the tiny interstices of the surface on which it is placed, thereby allowing intimate uniform contact between itself and that surface. This type of adhesiveness allows it to adhere to skin without employing additional chemical bonding agents, which permit the hydrogel to be removed from the skin without pain, skin damage or hair pulling and without leaving any residual components of the gel on the skin itself because the components are permanently bound within the gel structure.

Electrical Characteristics

The starting materials used to produce the hydrogel can be formulated with a wide range of amounts and types of ionic materials to produce hydrogels having highly desirable electrical characteristics. The uniform distribution of selected ions results in correspondingly reproducible electrical properties throughout the hydrogel, thereby lending itself to a wide variety of applications based on its conductive and capacitive properties. Furthermore, the predictable volume resistivity of the hydrogel lends itself to many critical physiological applications.

Electrolytes that can be used in the hydrogel include most cations, e.g., ammonium, sodium, potassium, lithium, magnesium, calcium, etc., and both simple and complex anions, e.g., chloride, sulfate, carbonates, nitrates, and anions of organic acids, e.g., acetic, citric, adipic, tartaric, lactic, propionic, glutaric and maleic acids, the latter being preferred in electrodes where corrosion of the metallic connector may be a problem. Magnesium acetate is especially suitable in this respect. The volume resistivity remains constant throughout the gels intended use, allowing virtually zero decay in the conductance of the skin in physiological applications, while allowing an upward even flow of skin excretions through the matrix away from the user. This change is uniform throughout the cross sectional area of the gel because of its balanced osmotic hydrophilic properties.

Unlike prior art material, the skin to which the gels of the invention are to be applied does not require prior abrasion or the prior application of an electrolyte before the hydrogels of the invention are applied to the skin. There is an unexpected benefit from the incorporation of glycerol in the hydrogels of the invention. It is predicted that the hydrogels of this invention more uniformly hydrate the stratum corneum and stabilize the stratum corneum as a conductive path.

An electrode of the invention may contain a conductive ink coating on the gel sheet face opposite that face to be applied to the skin.

Alternatively, a conductive scrim may be immersed in the hydrogel. As the conductive scrim immersed in the hydrogel there may be used a metallic scrim or a metallized polymeric scrim. The hydrogel may contain non-woven nylon with a metallic coating on its surface as an electroconductive scrim. Preferably, the electroconductive scrim is, e.g., a goldplated nylon mesh. It is possible to prepare an electrode of the invention with both a conductive ink and an electroconductive scrim in the hydrogel, but generally it is not necessary to use both.

It is also important to note that the hydrogels of the present invention have impedance values at 60 Hz of less than about 1,000 ohms, indeed, as low as about 15 ohms, at 0.1 mAmp of current measured peak to peak, when said impedance is measured for a pair of 4 cm×4 cm square gel sheets in face to face intimate contact with each other and in which the exposed face of each sheet is electrically coupled to a 1 cm diameter silver/silver chloride disc centered on the exposed surface. Any variations in electrical properties between sheets of hydrogels will be small on an absolute basis for a given standard deviation of impedance values. Such uniformity is very important because one would want the electrical properties of an electrode to be substantially the same as other electrodes which may also be in use on the same subject.

The electrical properties of particular embodiments of the present invention may be tested in accordance with tests that are enumerated in "Standard for Pregelled ECG Disposable Electrodes," Association for the Advancement of Medical Instrumentation (AAMI), Arlington, Va. (1984). These impedance measurements can be measured at any suitable frequency, e.g., 10 Hz to 5 MHz, using the configurations described in the AAMI reference.

Physical Properties

The basic sheet form of the hydrogel has both structural integrity along with resilient memory which permits it to return to and retain its original form when pressure is applied to the X-Y or Z axis. The product will withstand loss of water with a force of about 20 psi on a single surface, unlike other types of gels which exude water under the influence of gravity. Its high specific heat is another useful property. The hydrogel sheet is structurally unchanged and functional over a wide range of temperatures beyond its use range. The amount of energy required to raise the temperature of the sheet adds a safety margin in many physiological applications. It can also be useful in some combination therapy applications involving heat/cold and electrical stimulation.

Because the hydrogel sheet or film is produced with high energy radiation, such as that produced by an electron accelerator, it can be sterile at a sufficient dosage.

Particular advantages realized with electrodes employing the hydrogel are its stable electrical properties and its excellent adhesion to the skin. A superior physiological electrode should not store electrical charge, should have a low solution potential with the skin, and should be of low impedance. The hydrogels employed in the electrodes of this invention have all of these characteristics. The electrodes also adhere firmly to the skin, ordinarily without the necessity of external adhesive support, depending upon the duration of the application. Also, the surfaces of the hydrogel containing a humectant which are exposed to air during use slowly form a crust over a period of time, thereby preventing the bulk of the hydrogel film from drying out and acquiring altered electrical conductivity properties. The humectant also slows down the overall drying of the electrode. This is particularly useful for long term applications.

The electrodes of this invention also exhibit further superior properties upon removal after use. Although the electrodes readily adhere to the skin, they can very easily be removed therefrom in a painless manner without damaging the skin, as do conventional commercial adhesive products. Moreover, upon removal, the electrode leaves no visible residue on the skin, as do many liquid gel-based electrodes. In fact, liquid gel electrode materials must be wiped off the skin in a relatively painstaking manner, frequently by application of soap and water. Also, during application, the hydrogel of the electrodes of this invention does not stain or stick to clothing. All of these advantages are accomplished by employing ingredients which have an excellent history of biocompatibility so there is little likelihood of skin eruption or irritation.

Both sensing (detecting electrical signals on the skin) and working (transmitting electrical energy to the skin) electrodes according to this invention have numerous advantages over the prior art versions presently available commercially. Some of these are listed in Table II below.

TABLE II

| Property | | Advantage |
|---|---|---|
| 1. Thermal | Working: | Less chance of burns in ESU use. |
| | Sensing: | Less temp. drift in ECG/EEG use. |
| | Both: | Patient friendly; can be warmed to skin temp.; wide range of storage conditions acceptable. |
| 2. Adhesion | Working: | Less chance of radio frequency burns; better contact due to detachment in ESU use; adheres to paddle, no chance of a short due to movement in DEFIB. |
| | Sensing: | Less motion artifact in ECG/etc. Fewer false alarms due to detachment. |
| | Both: | No tapes, foams needed. |
| 3. Clarity | Working: | Able to see burns through ESU, TENS & DEFIB applications. |
| | Sensing: | Can detect local skin reactions. |
| | Both: | User preference, clean look. |
| 4. Impedance | Working: | Able to select medium impedance (by control of salt content) for EGU & DEFIB uses. |
| | Sensing: | Able to select low impedance for ECG/EEG/EMG/etc. applications. |
| 5. Uniform Impedance | Working: | No rf burns due to hot spots in ESU applications. No patient burns due to arcs in DEFIB applications. |
| | Sensing: | Low DC offset due to unmatched ECG electrodes. True signal reproduction in |

TABLE II-continued

| Property | | Advantage |
|---|---|---|
| | | relative EEG/EMG signals. |
| 6. Skin-Contact | Working: | Uniform application of power through skin in chance of & short due to movement DEFIB, ESU. ETC. |
| | Sensing: | Less noise in ECG/EEG use. |
| | Both: | Low surface impedance. |
| 7. Self-Sealing | Working: | Less edge effect in ESU use. No shorts due to product migration in chance of a short due to movement in DEFIB use. |
| | Sensing: | Low external pressure induced DC offset in ECG/EMG use. |
| | Both: | Can be cut to size. Less water loss in long term use. |
| 8. Conformability | Working: | Fewer burns at thin, boney sites in ESU use. Fewer arcs at hairy, thin, boney sites in DEFIB use. Fewer Air Gaps. |
| | Sensing: | Low motion induced artifact. Stays in place in ECG use. |
| 9. Bioburden | Both: | Very Low. |
| 10. Reusability | Both: | Can be easily rehydrated a number of times by moistening with water. |
| 11. Use Life | Both: | Slow dryout, maintains electrical properties, remains pliable |

VARIOUS ELECTRODE APPLICATIONS

An array of electrodes may be spatially arranged in a desired configuration on a flexible substrate. In an array of electrodes, the conductive substrates may be layered for shielding.

An electrode of the invention may be adapted for use on the surface of a mammal, e.g., the skin of a human. An electrode of the invention may be adapted for use on the skin of a human for non-medical biofeedback or biocontrol purposes or for medical diagnostic or therapeutic purposes.

The following is a description of specific end use applications of the ionic highly conductive hydrophilic sticky surfaced viscoelastic solid gels employed in the physiological electrodes of this invention and the advantages associated therewith.

TENS

The TENS (Transcutaneous Electrical Nerve Stimulation) electrode coupling media is produced from hydrogel sheets that have a low to medium ionic concentration, e.g., about 4 to 5 wt % of sodium chloride or magnesium acetate. It is used as a disposable interface between a "standard" reusable carbon electrode and the skin. The substance can also be used as an electrolyte in contact with its own carbon electrode material. The inert ingredients preclude skin irritation and the osmotic properties permit exudant to be carried away. The uniform ion control allows uniform current distribution, and the hydrophilic properties prevent any air-gaps that can cause alternating current rectification. The excellent adhesive characteristics prevent accidental partial detachment of the electrodes, and the consistent electrical properties assure continuous effective treatment. The cohesive properties allow the hydrogel sheet to be cut to size and easily removed from the skin and electrode, offering true ease of use. This also holds true of the totally disposable product where ease of use and no clean—up are controlling factors. Surprisingly, it is possible to use a TENS electrode of this invention for a period of time, remove it from the patient, wash it and reuse it on the patient for a number of subsequent times. Finally, the high specific heat and intimate contact become a deterrent to "hot spots" and any thermal burn potentials. The gel sheet's thermal sink properties and uniformity minimizes skin burns associated with the TENS procedure.

ESU

The ESU (Electro-Surgical Unit) electrode is produced from low ionic hydrogel sheet, e.g., 3–5 wt % NaCl. The dispersive radio frequency (grounding pad) return electrode application is a perfect conductive/adhesive application. The adhesive safety factor which prevents electrode removal and subsequent RF burns is of paramount importance. The precise ionic distribution and control prevents current pooling and small thermal burns. The hydrophilic properties lessen interference from surgical fluids and assures close physical contact, thereby preventing muscle stimulation from rectified current. The high specific heat provides another safety factor in diminishing edge effect heating and electrolyte drying. The hydrogel has an inherently uniform internal composition. Therefore, it is thermodynamically homogeneous and resists uneven gel or salt distribution during storage. Thus, electrodes manufactured from these hydrophilic gels do not suffer from gel or ingredient separation or gel migration, ensuring the presence of an adequate and uniform surface area for proper current dispersion from the body. The biological inertness of the hydrogel assures that local skin reactions, which could be confused with possible RF burn, will not be produced. The hydrogel's chemical inertness assures no ingredient breakdown via electrolysis, and the hydrogel's excellent response to elevated temperatures also assures performance under adverse use conditions. The gel sheet's thermal sink properties and uniformity minimizes skin burns associated with the ESU procedure.

EKG (ECG)

The hydrogel-based EKG (electrocardiogram) electrodes have the widest variety of specific use applications, made possible by the ability to produce hydrogels of specific ionic strength. A relatively high ion concentration, e.g., 7–8 wt % sodium chloride or potassium chloride, is chosen for high performance exercise use. A relatively low concentration, e.g., 5–6 wt % sodium chloride, is chosen for long term applications. The ability to use ions that have previously been hard to control allows the production of a near perfect electrode on a consistent basis. The unique ability of the hydrogel to be compressed without any associated signal drift makes it ideal for clinical situations. The bound hydrogel matrix provides a stable signal sensing electrolyte for consistent recording, regardless of changing skin or temperature conditions. The excellent adhesive properties of the hydrogel provides added safeguards against "lead-loss" alarm conditions and the cohesive component provides the sought after ease of use quality. The excellent biocompatability with skin makes it a perfect choice for long term contact. The hydrophilic characteristics allow good conduction without the patient discomfort of skin abrasives or shaving. The ability of the gel to be reapplied to a different site during use is another advantage. Finally, the excellent response to extreme temperatures makes EKG electrodes based on the hydrogels of this invention a good choice for emergency field applications.

DEFIBRILLATION

The defibrillator pad is produced from a sheet of medium ion percentage PEO gel, e.g., about 8 wt % NaCl or KCl. The pad is usually used as a conductive medium for the application of large amounts of electricity (voltage & current) and also used as a sensing electrolyte for EKG monitoring through the same electrodes. The excellent electrical properties allow efficient delivery of the therapeutic charge of electricity without a loss of monitoring capability due to its low DC offset. The bound polymer matrix prevents the product from pooling during storage and the unique thermal properties of the gel makes it the perfect choice for field use of these devices. the adhesive components assures proper paddle contact without the fear of electrode solution running, which allows repeated re-positioning or re-application of the paddles while maintaining effective skin contact. The hydrophilic properties of the gel sheet assure uniform skin contact without "pitting" and also eliminate the necessity of any significant skin preparation. The structural stability of the gel sheet allows greater user pressure upon paddle application without fear of pushing the gel away from the contact area. Finally, the clear glass-like property of the gel sheet allows full view of any trauma related injuries. The gel sheet's thermal sink properties and uniformity also minimizes skin burns associated with the defibrillation procedure.

BIOFEEDBACK AND BIOCONTROL

The biofeedback electrode is produced from a high concentration ionic gel sheet, e.g., 7–8 wt % NaCl or KCl. Advantageous characteristics of the hydrogel sheet are its ability to firmly adhere to the patient's skin because of its adhesiveness and its ability to be repositioned because of the cohesiveness. Its specific even ionic concentration allows it to be used with a wide variety of home and clinical electrodes, and permits immediate signal reception. The hydrophilic properties of the gel sheet allow many possible placement sites and repositioning without the need for any skin preparation. The biocompatibility and skin friendliness make long term use possible. The qualities of this product also find identical applications in the EEG, EMG, ENG and Evoked Potential fields. Specific electrical qualities necessary in all the above uses involve low noise potential and small DC offsets because of the low level signals involved. The gels bioinertness is especially important since these applications are frequently proximate to the eyes and mouth.

Currently, the biofeedback and biocontrol applications are the preferred applications for the gels of the invention and those the gels are preferably in the form of the electrodes which are mentioned above and illustrated in the FIGS. 1a, 1b, 2, 3, 4a and 4b.

Referring now more particularly to the FIGS., there is shown in FIG. 1a a top view of the inside of the headband 10, the side that in use is toward the forehead. Electrodes 1, 2, 3, 4, 5, 6 and 7 are removable replaceable hydrogel electrodes of this invention spatially arranged on the headband 10 so that their top surfaces shown are adapted to make electrical contact with the specific sensing spots on the subject's forehead in the case of electrodes 1 to 5 and with specific areas on the subject's cheeks in the case of electrodes 6 and 7. The bottom surfaces of hydrogel electrodes 1, 2, 3, 4, 5, 6 and 7 make electrical contact with areas of conductive ink on the substrate interface material, which is not clearly seen in FIG. 1b because of its small scale, but is more clearly shown in FIG. 2, which is discussed below. Making ultimate electrical contact with the hydrogel electrodes 1 to 7 through the conductive ink areas are electrical leads 1', 2', 3', 4', 5', 6' and 7', which are respectively attached to electrodes 1, 2, 3, 4, 5, 6 and 7. Headband 10 is comprised of three major components: foam interface forehead member 11, substrate member 12 and elastic rubber headband 13, which may be seen in FIG. 1b.

Figure 1B:
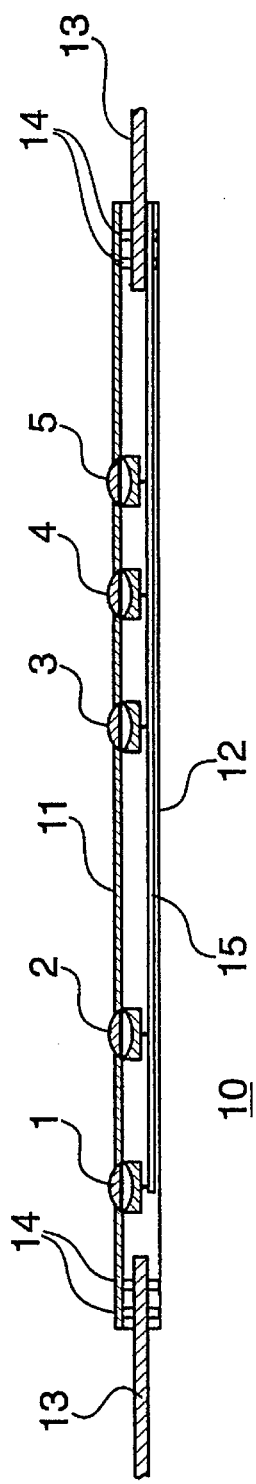

FIG. 1b is a cross section of a side elevation view of the headband of FIG. 1a. Foam interface forehead member 11 has means to attach the forehead hydrogel electrodes 1 to 5 in the desired locations for sensing signals from specific areas of the subject's forehead. Foam interface forehead member 11 may be formed from a strip of flexible, resilient polymeric foam. Substrate member 12 is generally of the same size and shape as foam interface forehead member 11 and may be made of a sheet of resilient polymeric material. The two members 11 and 12 are spaced apart by the thickness of an elastic rubber headband 13, each of whose ends is attached between the corresponding respective pair of ends of foam interface forehead member 11 and substrate member 12 by means of, e.g., mounting pins 14. In the channel thereby formed between forehead member 11 and spacing member 12, the electrical leads 1' to 7' enter wire harness jacket 15, which conveys the confluence of leads 1' to 7' as described in connection with the discussion of FIG. 3 below.

Figure 2:
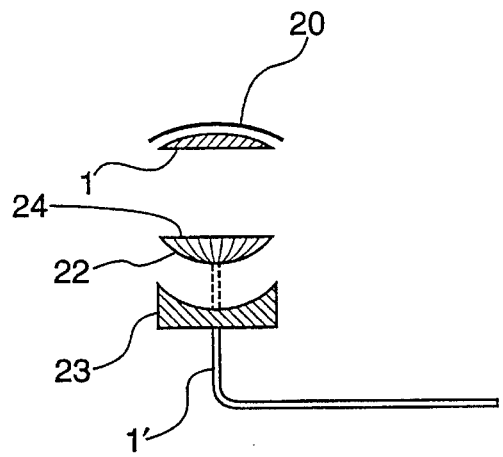
FIG. 2 is an exploded cross-sectional view of the electrode 1 of FIGS. 1a and b, which is constructed the same way as electrodes 2 to 7.

FIG. 2 is an exploded cross-sectional view of the hydrogel electrode 1 and associated elements of FIGS. 1a and b. Electrode 1 and its associated elements are constructed the same way as electrodes 2 to 7 and their associated elements. Consequently, this description applies equally to all of the electrodes 1 to 7. Vinyl release liner 20 functions to protect hydrogel 1 until it is used. The top surface of Conductive hydrogel 1 functions to make adhesive electrical interface between the headband and the forehead of the subject. Substrate interface material 22, which may be, e.g., a vinyl layer, has a conductive ink coating 24 on its uppermost surface that in use will make electrical contact with the bottom surface of the hydrogel electrode 1. The conductive ink coating 24 functions to make electrical interface between the hydrogel 1 and the insulated electrical lead 1', one end portion of which is embedded in substrate interface material 22 so that the exposed individual conductors of the multifilament conductor core of insulated electrical lead 1' are exposed at the surface of substrate interface material 22, coated with the conductive ink coating and thereby adapted to make electrical contact with conductive hydrogel 1. The other end of insulated electrical lead 1' passes through substrate base material 23 and in conjunction with the other insulated electrical leads 2' to 7' is conveyed as more specifically shown in FIG. 3.

Figure 3:
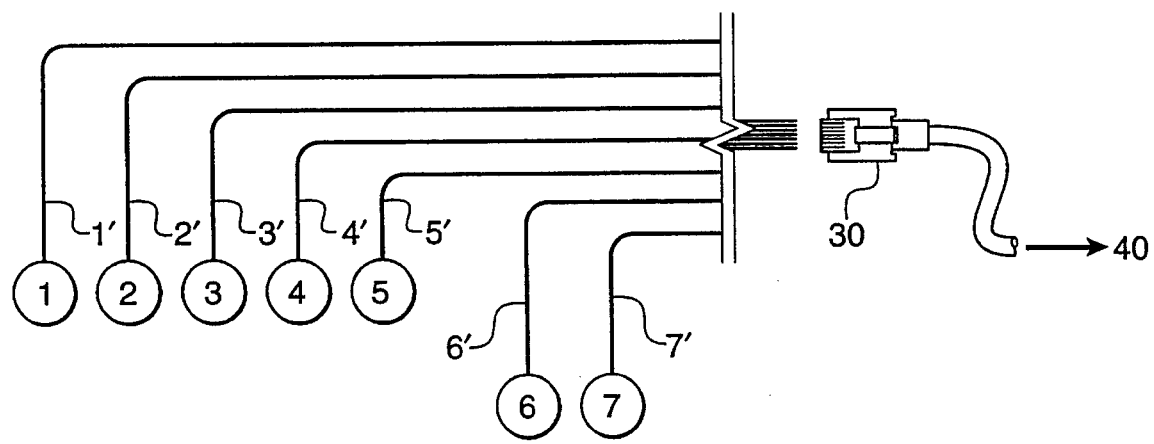
FIG. 3 is a schematic view of the electrical circuitry for the headband containing the electrodes of this invention.

FIG. 3 is a schematic view of the electrical circuitry for the headband which uses hydrogel electrodes of this invention. The electrodes 1 to 5 form the forehead interface, and electrodes 6 and 7 form the cheek interface. The respective insulated electrical leads 1' to 7' convey the electrical signals picked up by the electrodes 1 to 7 to a convenient interface male interface jack, e.g., a modular telephone jack 30, such as an RJ series jack, e.g., an RJ-63 jack. The interface jack 30 may be inserted in the corresponding female interface jack on the instrument or computer 40 (not shown) to which the electrical signals from the headband electrodes 1 to 7 are to be conveyed for processing.

Figure 4A:
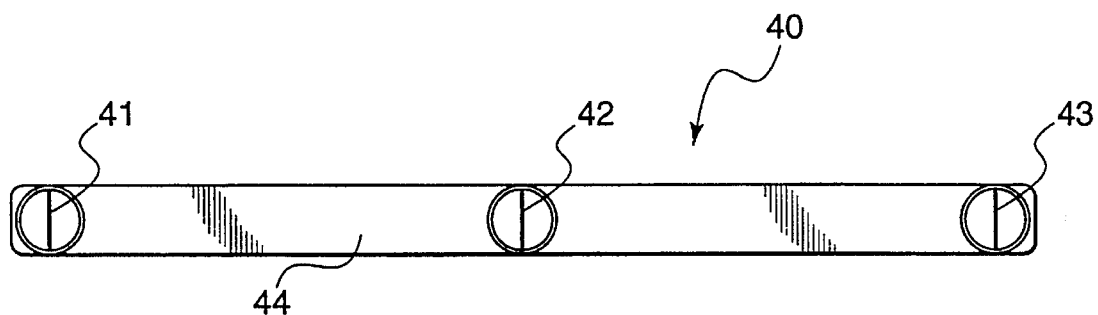
FIG. 4a is a top view of the inside of a replaceable headband electrode sensor module, the side that in use is toward the forehead.

There is shown in FIG. 4a a top view of the inside of a replaceable headband electrode sensor module 40, the side that in use is toward the forehead. For example, the sensor module 40 may be used as the foam interface forehead member 11, illustrated in FIGS. 1a and 1b. Sensor elements 41, 42, and 43 are hydrogel electrodes of the invention spatially arranged on the replaceable headband electrode carrier 44 so that they are adapted to make contact with specific sensing spots on the forehead.

Figure 4B:
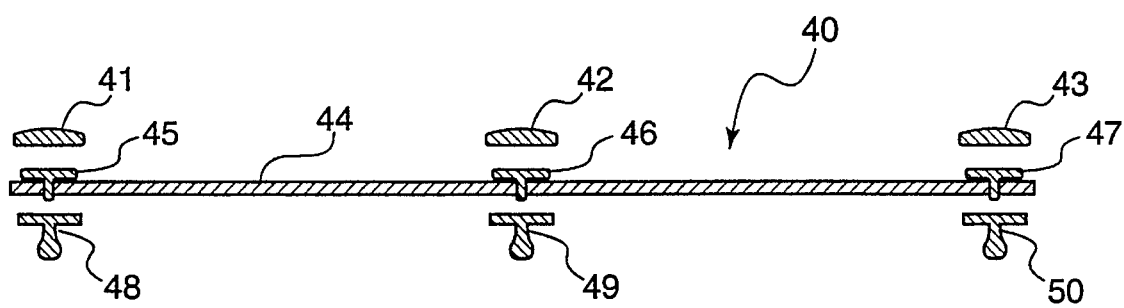

FIG. 4b is an exploded side view of the replaceable headband electrode sensor module 40, whose top view is shown in FIG. 4a. Making electrical contact with the sensor elements 41, 42 and 43 are the backsides of metal buttons 45, 46 and 47 respectively. The buttons 45, 46 and 47 are affixed to a carrier strip 44 so that the part of each button to be attached to a snap protrudes through the carrier strip 44. The carrier strip 44 may be made of any pliable material, e.g., a plastic foam strip. The snaps 48, 49 and 50 are positioned on a modular headband substrate member and are connected to conductor lead wires (not shown), and the conductor lead wires are connected to the biofeedback or biocontrol apparatus (not shown).

Although FIGS. 4a and 4b illustrate a sensor module for use in a headband, similar modules in different sizes and configurations may be used for biofeedback or biocontrol armbands, legbands, etc. Similar modular configurations may be used in other applications, e.g., for electrocardiograms, etc.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight, unless otherwise indicated.

EXAMPLE 1

A liquid film (ca. 50 mil) of a mixture of 9 wt % poly(ethylene oxide) (approximate weight average molecular weight 900,000), 5 wt % potassium chloride and about 0.3 wt % of selected biocides in water is cast (coated or extruded) onto a 2 mil film of polyethylene backing material. A polyethylene non-woven scrim (0.016 grams/inch$^2$) area weight is immersed into the viscous solution near its center. The scrim-containing solution is covered with a second sheet of 2 mil polyethylene film backing material, producing a sandwich 54 mils thick. This sandwich, held on a movable conventional conveyor belt, is then passed under the beam of a Van De Graaf generator, where it receives 0.7 Megarads of irradiation. The extrudable viscous aqueous mixture is thus converted to a sheet of solid viscoelastic hydrogel. One liner of said sheet is then removed, and a layer of glycerol is evenly applied to the exposed gel surface, so that the amount of glycerol added is 5 wt % of the unmodified gel sheet. The liner is then replaced, and the sheet is set aside in a horizontal orientation for a period of 24 hours.

A one inch square sheet is cut from the sandwich and the backing materials on both sides of the sheet are removed. The sheet of scrim-containing solid hydrogel is affixed to the back side of a conductive silver/silver chloride snap, the front of which is embedded in a sheet of adhesive polyurethane foam with the top of the snap protruding therefrom. This configuration of conductive hydrogel, silver/silver chloride button and polyurethane foam, constitutes a test electrode unit. Two identical such electrode units are then joined together hydrogel back to hydrogel back to form an electrode pair. The electrode pair is then tested to determine its electrical responses for use as a medical electrode. Two tests are done, using as a guideline the proposed standards for pregelled ECG disposable electrodes by the Association for the Advancement of Medical Instrumentation (*Standard for Pregelled ECG Disposable Electrodes*, Association for the Advancement of Medical Instrumentation, February 1984 Revision). The guideline values specified by the Association for such electrode pairs in the following electrical measurements are:

| Electrical Characteristic | Standard Values |
|---|---|
| (a) Initial offset voltage V(0) (MV) (This test is specified in the AAMI guidelines) | <100 |
| (b) Impedance at 60 Hz Z(60) (Ohm) (Analogous to the AAMI low frequency test: Impedance at 10 Hz) | <3000 |

Electrodes constructed using the method described herein were placed on the skin or exposed to air for a time interval of at least 24 hours with no substantial degradation in performance.

This long-term exposure is not practical without the addition of the humectant, as the gel will dry unacceptably, losing dimensional stability, acquiring a stiff crust, losing tack and irritating the skin.

EXAMPLE 2

The hydrogel of this example is similar to that of Example 1, except that the concentration of glycerol is raised to 15%.

EXAMPLE 3

The hydrogel of this example is similar to Example 1, except that a 5 wt % concentration of poly(ethylene glycol) is used in place of the glycerol.

EXAMPLE 4

The hydrogel of this example is similar to that of Example 3, except that the concentration of poly(ethylene glycol) is raised to 15%.

EXAMPLE 5

The hydrogel of this example is similar to that of Example 1, except that the aqueous mixture is comprised of a higher concentration of PEO (10.5 wt %), and the KCl is replaced with another conductive salt: 6.7 wt % Magnesium Acetate.

EXAMPLE 6

The hydrogel of this example is similar to that of Example 5, except that the concentration of glycerol is raised to 15%.

EXAMPLE 7

The hydrogel of this example is similar to Example 5, except that a 5 wt % concentration of poly(ethylene glycol) is used in place of the glycerol.

EXAMPLE 8

The hydrogel of this example is similar to that of Example 3, except that the concentration of poly(ethylene glycol) is raised to 15%.

TABLE III

Adhesion and electrical properties of non-drying gels.
Results shown before and after 24 hours exposure to air.

| Formulation | Z(60) (ohms) | | DC offset (mv) | | Tack Rolling Ball Method 3 (mm) | |
|---|---|---|---|---|---|---|
| | initial | 24 hrs | initial | 24 hrs | initial | 24 hrs |
| 9% PEO, 5% KCl, 5% glycerol | 54 | 30 | <10 | <10 | 3 | 7 |

TABLE III-continued

Adhesion and electrical properties of non-drying gels.
Results shown before and after 24 hours exposure to air.

| Formulation | Z(60) (ohms) | | DC offset (mv) | | Tack Rolling Ball Method 3 (mm) | |
|---|---|---|---|---|---|---|
| | initial | 24 hrs | initial | 24 hrs | initial | 24 hrs |
| 9% PEO, 5% KCl, 10% glycerol | 43 | 50 | <10 | <10 | 5 | 7 |
| 9% PEO, 5% KCl, 15% glycerol | 52 | 50 | <10 | <10 | 5 | 4 |
| 9% PEO, 5% KCl, 5% PEG 200 | ⁻53 | ⁻45 | <10 | <10 | ⁻5 | ⁻6 |
| 10.5% PEO, 6.7% MgAc, 5% glycerol | ⁻68 | ⁻56 | <20 | <20 | ⁻4 | ⁻6 |
| 10.5% PEO, 6.7% MgAc, 5% glycerol | ⁻72 | ⁻59 | <20 | <20 | ⁻4 | ⁻8 |

EXAMPLE 9

A liquid film (ca. 50 mil) of a mixture of 20 wt % poly(vinyl pyrrolidone) (approximate weight average molecular weight 1,000,000), 5 wt % sodium chloride and about 0.3 wt % of selected biocides in water is cast (coated or extruded) onto a 2 mil film of polyethylene backing material. A polyethylene non-woven scrim (0.016 grams/inch$^2$ area weight) is immersed into the viscous solution near its center. The scrim-containing solution is covered with a second sheet of 2 mil polyethylene film backing material, producing a sandwich 54 mils thick. This sandwich, held on a movable conventional conveyor belt, is then passed under the beam of a Van De Graaf generator, where it receives 2.0 Megarads of irradiation. The extrudable viscous aqueous mixture is thus converted to a sheet of solid viscoelastic hydrogel. One liner of said sheet is then removed, and a layer of glycerol is evenly applied to the exposed gel surface, so that the amount of glycerol added is 10 wt % of the unmodified gel sheet. The electrode pair assembly, testing and results are similar to those of example 1.

TABLE IV

Adhesion and electrical properties of non-drying gels
Results shown before and after 24 hours exposure to air.

| Formulation | Z(60) (ohms) | | DC Offset (mv) | | Tack Rolling Ball Method 3 (mm) | |
|---|---|---|---|---|---|---|
| | initial | 24 hrs | initial | 24 hrs | initial | 24 hrs |
| 20% PVP 5% NaCl, 10% glycerol | ⁻17 | ⁻25 | <10 | <10 | ⁻5 | ⁻10 |

The preceding examples can be repeated with similar results by substituting polyacrylamide and/or different operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A highly conductive hydrophilic gel composition comprising (a) a uniform aqueous solution of a water-soluble polymer crosslinked by high-energy irradiation in the essential absence of a humectant and an amount of a water-soluble electrolyte effective to reduce the transverse electrical resistance of said aqueous solution to an impedance at 60 Hz less than about 1,000 ohm, and (b) a humectant added to the aqueous solution after the water-soluble polymer is crosslinked, in an amount within the concentration of about 2 to about 15 wt % which is effective to retard the drying of the conductive hydrophilic gel composition when it is exposed to the atmosphere while being used.

2. The hydrophilic gel of claim 1 in which the water-soluble polymer is selected from the group consisting of poly(ethylene oxide), poly(vinyl pyrrolidone), polyacrylamide, and mixtures, blends and copolymers thereof.

3. The hydrophilic gel of claim 1 in which the gel is comprised of poly(ethylene oxide) in an amount of about 3 to about 35%.

4. The hydrophilic gel of claim 1 in which the gel is adhesive and is comprised of poly(ethylene oxide) in an amount of about 6 to about 18%.

5. The hydrophilic gel of claim 1 in which the gel is adhesive and is comprised of poly(ethylene oxide) in an amount of about 6 to about 12%.

6. The hydrophilic gel of claim 1, wherein the water-soluble polymer is a linear poly(ethylene oxide) having a molecular weight of about $0.2 \times 10^6$ Dalton to about $10 \times 10^6$ Dalton.

7. The hydrophilic gel of claim 1, wherein the water-soluble polymer is a linear poly(ethylene oxide) having a molecular weight of about $2 \times 10^6$ Dalton to about $6 \times 10^6$ Dalton.

8. The hydrophilic gel of claim 1, wherein the water-soluble polymer is a linear poly(ethylene oxide) having a molecular weight of about $0.8 \times 10^6$ Dalton to about $1.2 \times 10^6$ Dalton.

9. The hydrophilic gel of claim 1, wherein the gel is formed from a linear poly(ethylene oxide) that is crosslinked by a dose of high energy irradiation of from about 5 to about 20 KGy.

10. The hydrophilic gel of claim 1, wherein the water soluble polymer is poly(vinyl pyrrolidone) having a molecular weight of about $0.2 \times 10^6$ Dalton to about $4 \times 10^6$ Dalton.

11. The hydrophilic gel of claim 1, wherein the water soluble polymer is poly(vinyl pyrrolidone) having a molecular weight of about $0.6 \times 10^6$ Dalton to about $2 \times 10^6$ Dalton.

12. The hydrophilic gel of claim 1 in which the gel is comprised of poly(vinyl pyrrolidone) in an amount of about 8 to about 35%.

13. The hydrophilic gel of claim 1 in which the gel is comprised of poly(vinyl pyrrolidone) in an amount of about 12 to about 25%.

14. The hydrophilic gel of claim 1 in which the gel is comprised of poly(vinyl pyrrolidone) in an amount of about 15 to about 20%.

15. The hydrophilic gel of claim 1, wherein the gel is formed from a poly(vinyl pyrrolidone) that is crosslinked by a dose of high energy irradiation of from about 5 KGy to about 40 KGy.

16. The hydrophilic gel of claim 1, wherein the gel is formed from a poly(vinyl pyrrolidone) that is crosslinked by a dose of high energy irradiation of from about 5 KGy to about 50 KGy.

17. The hydrophilic gel of claim 1 in which said water-soluble electrolyte is an inorganic salt.

18. The hydrophilic gel of claim 1 in which said water-soluble electrolyte is present in the gel in an amount sufficient to reduce the transverse electrical resistance of said aqueous solution to an impedance at 60 Hz less than about 1,000 ohms and yet not sufficient to adversely affect the gel.

19. The hydrophilic gel of claim 1 in which said water-soluble electrolyte is selected from the group consisting of potassium salts, sodium salts, magnesium salts, calcium salts, and mixtures thereof.

20. The hydrophilic gel of claim 1 in which said water-soluble electrolyte is selected from the group consisting of potassium chloride, sodium chloride, magnesium sulfate, magnesium acetate, and mixtures thereof.

21. An electrode according to claim 1, wherein the electrolyte is a water soluble salt present in a concentration of about 0.1 to about 15 wt %.

22. An electrode according to claim 1, wherein the electrolyte is potassium chloride or sodium chloride in a concentration of about 0.1 to about 15 wt %.

23. The hydrophilic gel of claim 1 in which said transverse electrical impedance of said aqueous solution is reduced to an impedance at frequencies between about 10 to about 60 Hz of less than about 100 ohms.

24. The hydrophilic gel of claim 1 in which said humectant is glycerol, sorbitol, poly(ethylene glycol), propylene glycol, or poly(propylene glycol).

25. The hydrophilic gel of claim 1 in which the humectant is a mixture of glycerol and one or more of the poly(ethylene glycols) or propylene glycol.

26. The hydrophilic gel of claim 1 in which as the humectant glycerol or poly(ethylene glycol) is present in the gel at a total concentration of from about 2 to about 15%.

27. The hydrophilic gel of claim 1 in which as the humectant glycerol or poly(ethylene glycol) is present in the gel at a total concentration of from about 7 to about 13%.

28. The hydrophilic gel of claim 1 which further comprises an additive uniformly dispersed therein.

29. The hydrophilic gel of claim 1 which further comprises an additive uniformly dispersed therein selected from the group consisting of preservatives, stabilizers, fire retardants, pigments, refractive particles, bactericides, antibiotics, cosmetics, moisturizers, pharmaceuticals, and mixtures thereof.

30. The hydrophilic gel of claim 1 which further comprises a biocide uniformly dispersed therein.

31. The hydrophilic gel of claim 1 which further comprises a low area-weight scrim in intimate contact therewith.

32. The hydrophilic gel of claim 1 which further comprises a low area-weight scrim which is manufactured from a synthetic water-insoluble polymer in initmate contact with the hydrophilic gel.

33. A physiological electrode adapted for providing electrical contact with a surface of a sentient creature and comprising:

a. means for interfacing with a surface of a sentient creature comprising a sheet of a conductive viscoelastic hydrophilic gel composition, wherein the hydrophilic gel composition is a homogeneous aqueous mixture, substantially free of unbound water, monomers and cross-linking agents, the hydrophilic gel composition comprising:

i. A uniform aqueous solution of a water-soluble polymer cross-linked by high energy irradiation in the essential absence of a humectant, ii. a water-soluble electrolyte in an amount sufficient to reduce the transverse electrical impedance of said aqueous solution to an impedance at 60 Hz of less than about 1000 ohm, iii. a humectant added to the hydrophilic gel composition after it is crosslinked, in an amount within a concentration of about 2 to about 15 wt %, which is sufficient to retard the drying of the conductive hydrophilic gel composition, to keep it soft and pliable when it is exposed to the atmosphere or being used, and b. a conductive member including means for connecting the physiological electrode to an external electrical apparatus;

said means for interfacing with a surface of a sentient creature (a) connected electrically with the conductive member (b) and having a face adapted for interfacing electrically with the surface of the sentient creature to which it is affixed, which gel sheet is more cohesive than it is adhesive to the surface of the sentient creature and is mechanically connected more firmly to the conductive member (b) than it can be adhesively affixed to the surface of the sentient creature, thereby enabling concurrent removal of the conductive member (b) and the means for interfacing with a surface of a sentient creature (a) from the surface of the sentient creature after use without leaving a noticeable polymeric residue on the surface of the sentient creature.

34. An electrode according to claim 33, wherein the water-soluble polymer is poly(ethylene oxide), poly(vinyl pyrrolidone), or polyacrylamide.

35. An electrode according to claim 33, wherein poly(ethylene oxide) is the water-soluble polymer in the hydrophilic gel composition and is present in a concentration of about 3 to about 25 wt %.

36. An electrode according to claim 33, wherein poly(ethylene oxide) is the water-soluble polymer in the hydrophilic gel composition and is present in a concentration of about 6 to about 12 wt %.

37. An electrode according to claim 33, wherein linear poly(ethylene oxide) is the water-soluble polymer and has a molecular weight of about $0.2 \times 10^6$ to about $10 \times 10^6$ Daltons.

38. An electrode according to claim 33, wherein the electrolyte is a water soluble salt present in a concentration of about 0.1 to about 15 wt %.

39. An electrode according to claim 33, wherein the electrolyte is selected from the group consisting of potassium salts, sodium salts, magnesium salts, calcium salts, and mixtures thereof.

40. An electrode according to claim 33, wherein the electrolyte is potassium chloride, sodium chloride or magnesium acetate in a concentration of about 0.1 to about 15 wt %.

41. An electrode according to claim 33, wherein the humectant is glycerol, sorbitol, poly(ethylene glycol), propylene glycol, or poly(propylene glycol).

42. An electrode according to claim 33, wherein glycerol is present in the hydrophilic gel composition in a concentration of about 2 to about 20 wt %.

43. An electrode according to claim 33, wherein glycerol is present in the hydrophilic gel composition in a concentration of about 7 to about 13 wt %.

44. An electrode according to claim 33, wherein a conductive ink coating is on the gel sheet face opposite that face to be applied to the skin.

45. An electrode according to claim 33, wherein a low area-weight scrim is immersed in the hydrophilic gel composition.

46. An electrode according to claim 33, wherein a low area-weight scrim comprised of a sheet of non-woven polyethylene is immersed in the hydrophilic gel composition.

47. An electrode according to claim 33, wherein a conductive scrim is immersed in the hydrophilic gel composition.

48. An electrode according to claim 33, wherein immersed in the hydrophilic gel composition is a metallic scrim or a metallized polymeric scrim which does not undesirably corrode in the use intended for the electrode.

49. An electrode according to claim 33, wherein immersed in the hydrophilic gel composition is a nylon scrim plated with a noble metal.

50. An electrode according to claim 33, wherein immersed in the hydrophilic gel composition is a gold-plated nylon scrim.

51. An electrode according to claim 33, wherein the face of the interfacing means (b) adapted for interfacing with a human's skin is covered by a protective backing sheet which is peelably removable therefrom.

52. An electrode according to claim 33, wherein a low area-weight scrim is immersed in the hydrophilic gel composition; wherein the electrolyte is a water-soluble salt present in a concentration of about 0.1 to about 15 wt %; wherein the water-soluble polymer is linear poly(ethylene oxide) that has a molecular weight of about 0.5 to about $5 \times 10^6$ Daltons and is present in the hydrophilic gel composition at a concentration of about 4 to about 25%; wherein glycerol is present in the hydrophilic gel composition in a concentration of about 2 to about 10%; and wherein the face of the sheet adapted for interfacing with the sentient creature's skin is covered by a backing sheet which is peelably removable therefrom.

53. An electrode according to claim 33, wherein the water-soluble polymer is linear poly(ethylene oxide), has a molecular weight of about 0.5 to $5 \times 10^6$ Daltons and is present in the hydrophilic gel composition at a concentration of about to about 25 w %; wherein as the electrolyte potassium chloride or sodium chloride is present in the hydrophilic gel composition in a concentration of about 0.1 to about 10 w %; wherein glycerol is present in the hydrophilic gel composition in a concentration of about 2 to about 10 w %; wherein a low area-weight scrim formed of a sheet of non-woven polyethylene is immersed in the hydrophilic gel composition; and wherein the face of the sheet that is adapted for interfacing with a human's skin is covered by a release sheet which is peelably removable therefrom.

54. An array of electrodes as claimed in claim 33, wherein the electrodes are spatially and removably arranged in a desired configuration on a flexible polymeric substrate adapted to be placed conformably on the surface of a sentient creature so that the electrodes are in contact with the desired areas of the surface of the sentient creature.

55. An array of electrodes according to claim 33, wherein the individual electrodes are layered for shielding and signal transmission.

56. A modular band comprised of a sensor module and a substrate module, the sensor module being comprised of an array of conductive hydrogel electrodes as claimed in claim 33, spatially arranged on the sensor module so that the electrodes are adapted to make contact with specific sensing spots on a sentient being, an electrical connector being attached to each electrode, the substrate module being adapted to maintain the sensor module in the desired contact with the sentient being.

57. A modular headband comprised of a sensor module and a substrate module, the sensor module being comprised of an array of conductive hydrogel electrodes as claimed in claim 33, spatially arranged on the sensor module so that the electrodes are adapted to make contact with specific sensing spots on the forehead of a mammal in the case of most of the electrodes and with specific areas on at least one cheek in the case of at least one electrode, an electrical connector being attached to each electrode, the substrate module being adapted to maintain the sensor module in the desired contact with a mammal.

* * * * *